(12) United States Patent
Misner et al.

(10) Patent No.: US 11,028,359 B2
(45) Date of Patent: Jun. 8, 2021

(54) SEPARATION DEVICES, ASSOCIATED METHODS, AND SYSTEMS

(71) Applicant: GLOBAL LIFE SCIENCES SOLUTIONS USA LLC, Marlborough, MA (US)

(72) Inventors: Matthew Jeremiah Misner, Delanson, NY (US); Rachel Marie Gettings, Albany, NY (US); Christine Angela Morton, Mechanicville, NY (US); Erik Leeming Kvam, Niskayuna, NY (US); Jason William Castle, Esperance, NY (US); Anindya Kanti De, Bangalore (IN); Jared Timothy Hale, Ballston Lake, NY (US); Craig Patrick Galligan, Niskayuna, NY (US); Vincent Francis Pizzi, Millis, MA (US)

(73) Assignee: GLOBAL LIFE SCIENCES SOLUTIONS USA LLC, Marlborough, MA (US)

(*) Notice: Subject to any disclaimer, the term of this patent is extended or adjusted under 35 U.S.C. 154(b) by 100 days.

(21) Appl. No.: 16/128,121

(22) Filed: Sep. 11, 2018

(65) Prior Publication Data
US 2020/0080047 A1  Mar. 12, 2020

(51) Int. Cl.
*B01D 17/02* (2006.01)
*B01D 21/00* (2006.01)
(Continued)

(52) U.S. Cl.
CPC ............. *C12M 47/02* (2013.01); *B01D 17/02* (2013.01); *B01D 21/0015* (2013.01);
(Continued)

(58) Field of Classification Search
CPC ...... C12M 47/02; C12M 23/12; C12M 23/40; C12M 33/22; C12M 23/28; C12M 23/26;
(Continued)

(56) References Cited

U.S. PATENT DOCUMENTS 3,709,361 A   1/1973 Miller
4,737,268 A   4/1988 Giddings
(Continued)

FOREIGN PATENT DOCUMENTS

WO   2013109520 A1   7/2013
WO   2013124326 A1   8/2013

OTHER PUBLICATIONS

Falconer, Andrew; "Gravity Separation: Old Technique/New Methods", Physical Separation in Science Engineering, 2003, vol. 12, No. 1, pp. 31-48.
(Continued)

*Primary Examiner* — Benjamin L Lebron
(74) *Attorney, Agent, or Firm* — Jeff B. Vockrodt; Culhane Meadows, PLLC

(57) ABSTRACT

A system for isolating a target molecule from a bioprocess fluid includes a single-use disposable separation device having a plurality of perimeter-bonded layers defining one or more mesofluidic channels of the separation device, wherein each layer includes a biocompatible polymer material, wherein the separation device is configured to separate at least a portion of particles from the bioprocess fluid to generate a substantially clarified bioprocess fluid, and a chromatography system fluidically coupled at the outflow of the separation device in a configuration for further processing the clarified bioprocess fluid.

29 Claims, 12 Drawing Sheets

(51) Int. Cl.
  *B01D 21/02* (2006.01)
  *B01D 21/24* (2006.01)
  *B01L 3/00* (2006.01)
  *C12M 1/00* (2006.01)
  *C12M 1/26* (2006.01)
  *G01N 30/00* (2006.01)
  *C12M 1/32* (2006.01)

(52) U.S. Cl.
  CPC ......... *B01D 21/0087* (2013.01); *B01D 21/02* (2013.01); *B01D 21/2461* (2013.01); *B01L 3/502761* (2013.01); *C12M 23/12* (2013.01); *C12M 23/28* (2013.01); *C12M 23/40* (2013.01); *C12M 33/22* (2013.01); *G01N 30/00* (2013.01); *B01D 2257/91* (2013.01); *B01J 2219/00166* (2013.01); *B01L 2200/0631* (2013.01); *B01L 2200/0668* (2013.01); *B01L 2300/0681* (2013.01); *B01L 2400/0487* (2013.01); *C12M 23/14* (2013.01); *C12M 23/26* (2013.01)

(58) Field of Classification Search
  CPC ...... C12M 23/14; C12M 23/06; C12M 29/04; C12M 27/16; B01D 17/02; B01D 21/087; B01D 21/02; B01D 21/2461; B01D 2257/91; B01D 24/001; B01D 24/007; B01D 24/02; B01D 24/24; B01D 21/0015; B01D 21/0045; B01D 21/0057; B01D 21/009; B01D 21/2488; B01D 21/0039; B01L 3/502761; B01L 2300/0681; B01L 2400/0487; G01N 30/00; B01J 2219/00166
  See application file for complete search history.

(56) References Cited

U.S. PATENT DOCUMENTS

| | | | |
|---|---|---|---|
| 4,950,389 A | 8/1990 | Plat et al. | |
| 4,994,176 A | 2/1991 | Yakunin et al. | |
| 5,273,904 A | 12/1993 | Langley | |
| 5,616,831 A | 4/1997 | Ferland et al. | |
| 5,817,505 A | 10/1998 | Thompson et al. | |
| 7,094,354 B2 | 8/2006 | Pugia et al. | |
| 7,429,332 B2 | 9/2008 | Surjaatmadja et al. | |
| 7,939,034 B2 | 5/2011 | Shiraishi et al. | |
| 8,276,760 B2 | 10/2012 | Lean et al. | |
| 8,308,959 B2 | 11/2012 | Noles | |
| 8,858,079 B2 | 10/2014 | Jiang et al. | |
| 9,533,241 B2 | 1/2017 | Presz, Jr. et al. | |
| 9,550,016 B2 | 1/2017 | Gifford | |
| 9,594,071 B2 | 3/2017 | Hart et al. | |
| 9,808,803 B2 | 11/2017 | Toner et al. | |
| 9,840,691 B2 | 12/2017 | Paster et al. | |
| 2008/0093306 A1 | 4/2008 | Oakey et al. | |
| 2010/0093078 A1 | 4/2010 | Wang et al. | |
| 2013/0012689 A1* | 1/2013 | Singh | B01D 15/3809 530/388.1 |
| 2015/0017716 A1* | 1/2015 | Kauling | C12M 33/22 435/325 |
| 2016/0312168 A1* | 10/2016 | Pizzi | C12M 47/02 |
| 2017/0153210 A1 | 6/2017 | Eriksson et al. | |
| 2018/0001231 A1 | 1/2018 | Puleo et al. | |
| 2018/0135006 A1 | 5/2018 | Maiser et al. | |

OTHER PUBLICATIONS

Yi, C., et al; "Microfluidics Technology for Manipulation a Analysis of Biological Cells", Analytica Chimica Acta 560, 2006, pp. 1-23.
Zydney, Andrew L.; "Continuous Downstream Processing for High Value Biological Products: A Review", Biotechnology and Bioengineering, vol. 113, No. 3, Mar. 2016, pp. 465-475.
Maia, Amazile B.R.A.; "Application of Gravitational Sedimentation to Efficient Cellular Recycling in Continuous Alcoholic Fermentation", Biotechnology and Bioengineering, vol. 41, p. 361-369, 1993.
Woodside, Steven M., et al.; "Mammalian cell retention devices for stirred perfusion bioreactors", Cytotechnology, vol. 28, Issue: 1-3, pp. 163-175, Nov. 1998.
Kuroda, Chiaki, et al.; "Microfluidic sedimentation system for separation of plasma from whole blood", Sensors, 2014 IEEE, Nov. 2-5, 2014.
International Written Opinion and Search Report corresponding to International Application No. PCT/EP2019/073198, dated Feb. 21, 2020.

* cited by examiner

SEPARATION DEVICES, ASSOCIATED METHODS, AND SYSTEMS

BACKGROUND

The present disclosure relates to systems and devices comprising mesofluidic channels useful for separating particulate materials from fluids. In a particular aspect, the present disclosure relates to a method for separating particulates using the systems and devices provided herein.

Biopharmaceutical production is trending toward higher cell densities and product titers such that single-use harvest systems are becoming financially and logistically advantageous. Single-use bioreactors for cell culture volumes greater than or equal to 2,000 L provide an economically attractive alternative to stainless steel infrastructure as batch production titers continue to increase. Many biopharmaceuticals are initially separated from producer cells in a crude harvest step prior to downstream purification via chromatography systems. Volumetrically scalable solutions for this harvest step include centrifugation and/or depth filtration when a protein or other product (e.g. virus) is produced. Depth filtration has been adopted as a single-use harvest method to remove intact cells and cellular debris via primary and secondary clarification, respectively, however this process suffers from cell caking and clogging as bioreactor cell densities gradually increase, which is undesirable for manufacturing productivity. Additionally, the total filtration area of depth filtration tends to scale proportionally with cell density for primary harvest, which is undesirable for inventory floor space and is technically and economically prohibitive at cell densities greater than 30 million cells/mL. Centrifugation may be a suitable alternative for large fixed-asset (stainless steel) manufacturing sites, however, centrifugation may be prohibitive in smaller single-use contexts due to capital equipment expenditure, sterilization preparation time between batches, and centrifugation equipment maintenance. Additionally, centrifugation-based harvest may suffer from unsatisfactory product loss when bioreactor feedstocks contain high cell densities (e.g. solids exceeding 10% of the culture mass). Past attempts to address cell separation typically employ inclination that includes vertically flowing cell containing fluid at an angle between 30 and 80° from horizontal toward a separation channel. Cell separation is transverse to the vertical fluid flow through separation channel for cells to flow into a separate chamber. Separation is limited to the cells passing over the separation channel amounting to a filtration device, prone to fouling, for perfusion operations with flow rates below 40 L/day, which is not applicable to batch cell culture primary clarification operations.

As such, there exists a need to provide devices and methods for efficient separation of cells and/or dispersed particulates (including cell aggregates, adhered cells on carriers, resin beads and diatomaceous earth) from fluids, especially from bioreactor feedstocks with high cell densities. Fast and efficient separation and collection of cells and/or particulates from large samples (e.g., ≥2,000 L), without complex equipment, remains an unmet need.

BRIEF DESCRIPTION

In one embodiment, a method for clarifying a bioprocess fluid having particles suspended in a cell culture fluid includes flowing an unclarified bioprocess fluid from a bioreactor through a plurality of mesofluidic channels within a separation device to separate at least a portion of particles from the unclarified bioprocess fluid to generate a substantially clarified bioprocess fluid, and collecting the clarified bioprocess fluid from an outlet of the separation device, wherein a residence time of the bioprocess fluid within the separation device ranges from 10 minutes to 40 minutes relative to the time at which all or a portion of the fluid first enters the device.

In another embodiment, a system for isolating a target molecule from a bioprocess fluid includes a single-use disposable separation device having a plurality of perimeter-bonded layers defining one or more mesofluidic channels of the separation device, wherein each layer includes a biocompatible polymer material, wherein the separation device is configured to separate at least a portion of particles from the bioprocess fluid to generate a substantially clarified bioprocess fluid, and a chromatography system fluidically coupled at the outflow of the separation device in a configuration for further processing the clarified bioprocess fluid.

In another embodiment, a system for isolating a target molecule from a bioprocess fluid includes a bioreactor, a separation device fluidically coupled to the bioreactor at an inlet of the separation device and configured to receive bioprocess fluid from the bioreactor and to separate a least a portion of particles from the bioprocess fluid to generate a substantially clarified bioprocess fluid, wherein the separation device includes a plurality of parallel mesofluidic channels for separation of the particles, and wherein each mesofluidic channel of the plurality of mesofluidic channels includes a height within a range of 2 millimeters to 20 millimeters, and one or more additional purification subsystems fluidically coupled to an outlet of the separation device and configured for further processing of the clarified bioprocess fluid, wherein the additional purification subsystems include chromatographic separation, secondary depth filtration, a polishing membrane, or any combination thereof.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
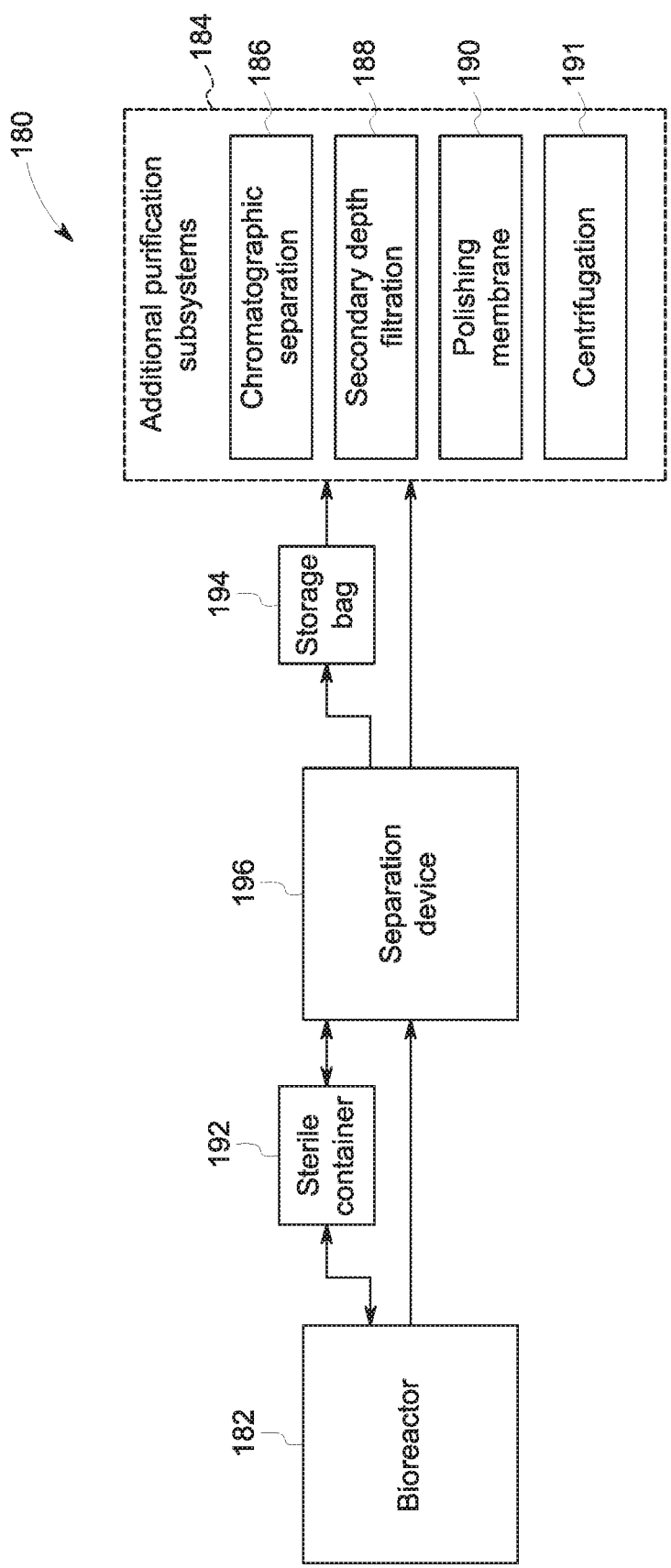
FIG. 1 illustrates a schematic diagram of an embodiment of a bioprocessing system including a separation device, in accordance with aspects of the present disclosure.

In some embodiments discussed herein, a separation device may be used for harvesting or clarifying cell culture fluid in a biopharmaceutical process. In such processes, the target substance to be recovered from the fluid containing particles such as cells may be a clarified fluid, the separated particles, or a combination thereof. With the foregoing in mind, FIG. 1 illustrates a bioprocessing system 180 including a separation device 196 for separating and recovering a clarified base fluid, separated particles, or a combination thereof.

The bioprocessing system 180 may include a bioreactor 182 in which a biological reaction or process is carried out, or any other device or system that facilitates a biologically active environment. In some embodiments, after a reaction has taken place within the bioreactor 182, an unclarified solution of a base fluid containing cells and/or other dispersed particulates may be flowed from the bioreactor 182 to the separation device(s) 196. The device 196 may be used to separate the cells and/or other particulates out of the base fluid. As such, as the solution is flowed through the separation device at a defined flow rate, the device 196 may trap or contain the cells and/or other particulates, such as cells, aggregated cells, adhered cells on carriers, diatomaceous earth, resin beads, or a combination thereof, that fall out of the solution to generate a substantially clarified fluid, as discussed in greater detail with respect to FIG. 2, which may contain the target of the bioprocess. The clarified fluid may contain cells, biotherapeutically active products, viruses, vaccines, deoxyribonucleic acid (DNA), ribonucleic acid (RNA), or a combination thereof. In some embodiments, the clarified fluid may exit the device 196 and may be flowed through one or more additional devices 196 (e.g., a series of devices 196) or may be flowed through one or more additional purification subsystems 184 of the bioprocessing system 180 to further clarify or purify the clarified fluid, such as a chromatographic separation subsystem 186, a secondary depth filtration system 188, a polishing membrane subsystem 190 (e.g., membrane filtration subsystem), a centrifugation subsystem 191, or any other purification subsystem.

The device 196 may be a single-use disposable device, which may already be sterile and therefore eliminate steps for cleaning and sterilizing on the biopharmaceutical production floor. The device 196 may each be made of rigid or flexible material, such as a rigid or flexible plastic, or may be made of both rigid and flexible materials. FIGS. 2-5 show separation devices with a relatively rigid structure, while the devices illustrated below in FIG. 7-11 show separation devices with a relatively flexible structure. The material used to form some or all of the separation device body or interior may be any high density plastic or polymer, such as high density polyethylene, polypropylene, or ethylene vinyl acetate copolymers.

In some embodiments, if the cells and/or other particulates that sediment out of the solution within the device 196 are the intended product of the bioprocess using the bioprocessing system 180, the cells and/or other particulates may be recovered from the device 196. Once the unclarified solution is flowed through the device 196 such that the cells and/or other particulates sediment from the solution, and before a terminal retention capacity of the device is reached, a common or separate fluidic conduit fluidically coupled to an inlet of the device 196 may be operated to flush out product contained in the device to improve product recovery and increased product yield.

In some embodiments, if the cells and/or other particulates that sediment out of the solution within the device 196 are the intended product of the bioprocess using the bioprocessing system 180, the cells and/or other particulates may be recovered from the device 196. Once the unclarified solution is flowed through the device 196 such that the cells and/or other particulates sediment from the solution, and before a terminal retention capacity of the device is reached, a common or separate fluidic conduit fluidically coupled to an outlet of the device 196 may be operated to reverse the flow within the device 196 from the outlet to an inlet of the device. The reverse flow may return the cells and/or other particulates retained within the device 196 (e.g., retentate) to the bioreactor 182 and/or a separate sterile container 192 fluidically coupled to the device 196 and/or the bioreactor 182.

In some embodiments, if the cells and/or other particulates that sediment out of the solution within the device 196 are the intended product of the bioprocess using the bioprocessing system 180, the cells and/or other particulates may be recovered from the device 196. Once the unclarified solution is flowed through the device 196 such that the cells and/or other particulates sediment from the solution, and before a terminal retention capacity of the device is reached, the fluid of the retained cells and/or other particulates may be exchanged with an alternate compatible fluid, such as a buffer or media. Engagement of a common or separate fluidic conduit fluidically coupled to an outlet of the device 196 may be operated to reverse the flow using the same or alternate compatible fluid within the device 196 from the outlet to an inlet of the device. The reverse flow may return the cells and/or other particulates retained within the device 196 (e.g., retentate) to the bioreactor 182 and/or a separate sterile container 192 fluidically coupled to the device 196 and/or the bioreactor 182.

Additionally or alternatively, in some embodiments, the bioprocessing system 180 may be operated in a manner that may cause the cells and/or other particulates within the unclarified solution to sediment out of the unclarified solution more rapidly within the device 196 and thus, increase the efficiency of the device 196 and the bioprocessing system 180 as a whole. For example, in some embodiments, the pH of the solution may be adjusted prior to entering the device 196. A fluid or other material may be added to the bioreactor 182 to adjust the pH, which may be monitored, within of the solution within the bioreactor 182 via an inlet into the bioreactor 186. The pH may be lowered to, for example, 4.5-5 pH before being flowed through the device 196. A lower pH may cause the cells and/or other particles in the solution to accumulate (e.g., flocculate) into large aggregates, allowing the cells and/or other particles to fall out of the solution more rapidly within the separation device 196 to produce a more clarified fluid product. The pH of the clarified fluid from the device 196 may be neutralized back to the starting pH of the solution, for example 7 pH, by addition of a base into the device 196 or an additional storage bag 194, before recovery or before being further clarified using one or more of the additional purification subsystems 184. In some embodiments, additional particles or additives may be added to the cell culture fluid (e.g., the unclarified solution) to aid in improving settling performance of the device 196. For example, a flocculant, such as poly(diallyldimethylammonium chloride (PDADMC) or diatomaceous earth (DE), may be added to the cell culture fluid. The flocculant may aggregate the particles, as well as other debris in the cell culture fluid, into larger particles, which may settle faster based on the density difference between the larger particles and the fluid of the cell culture fluid. This in turn may improve separation performance of the device 196, especially at higher particle densities (e.g., cell densities). In some embodiments, the larger particles may be recovered from the device 196. In such embodiments, a net charge of the added flocculant may also be used to capture charged species in the cell culture fluid, such as DNA or host-cell protein (HCP).

Figure 2:
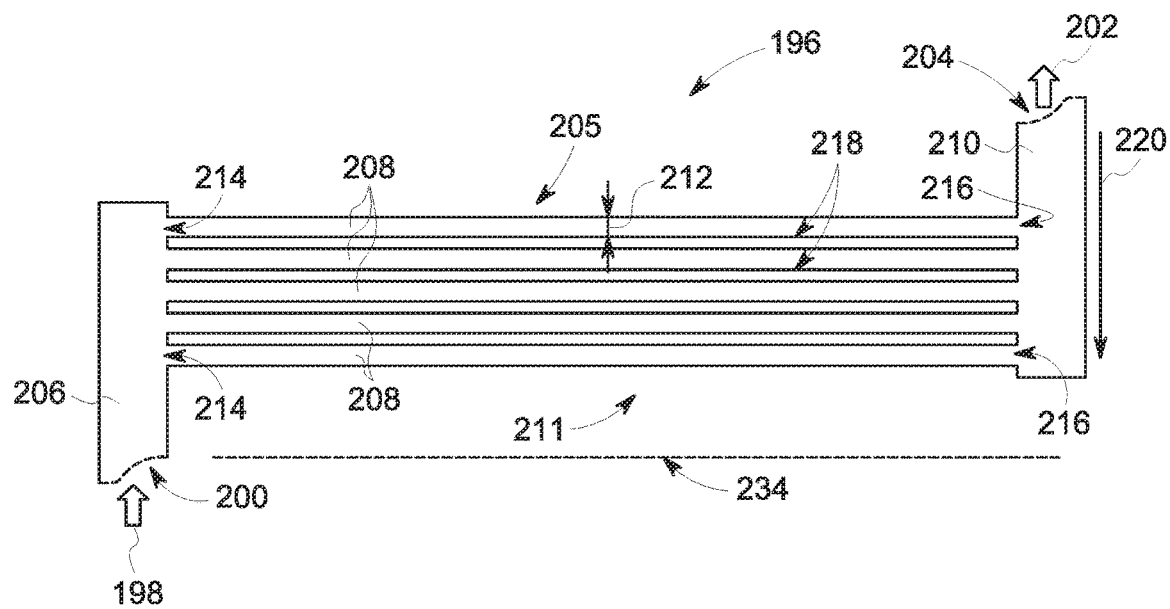
FIG. 2 illustrates a schematic representation of a side view of an embodiment of the separation device of FIG. 1, in accordance with aspects of the present disclosure.

FIG. 2 illustrates an embodiment of the separation device 196 (e.g., a non-inclined settler configured to be operated in a horizontal or substantially horizontal orientation) that may be used to separate the cells and/or particles from a base fluid of the solution. In preferred embodiments, the device 196 operationally functions through balancing the time a particle resides in the device 196 as it flows through against the time it takes for a particle to settle by gravity in the device to achieve a settling efficiency. Specifically, if the flow rate of the particle containing fluid through the device of a given volume allows for a residence time that is greater than the particle settling time, the particle will be captured. If the flow rate of the particle containing fluid results in a residence time less than the particle settling time, the particle will not be efficiently retained. The residence time is simply calculated by dividing the device volume by flow rate.

The device 196 may receive an input of a cell culture fluid 198 (e.g., the unclarified solution containing cells and/or other particles suspended in a base fluid), such as a cell suspension, or other fluid containing particles, via a fluid inlet 200. The device 196 may receive the cell culture fluid 198 from the bioreactor 182, or other source, at a particular flow rate. The device 196 may be an assisted gravity settler used to separate particles, such as cells and/or other particles, from the cell culture fluid 198 to allow for recovery of a clarified fluid 202 via a fluid outlet 204 of the device 196. A target product of the harvest process may be contained within the recovered clarified fluid 202.

A body 205 of the device 196 may include a fluid inlet manifold 206, multiple mesofluidic channels 208 (e.g., channels having heights within the millimeter to centimeter range), and a fluid outlet manifold 210. The fluid inlet manifold 206 may couple the fluid inlet 200 to the multiple mesofluidic channels 208. The device 196 may include any number of mesofluidic channels 208 (e.g., 2, 3, 4, 5, 6, etc.) arranged in a stacked or parallel configuration, as shown in the illustrated embodiment, providing a series of stacked mesofluidic channels in a separation portion 211 of the body 205 of the device 196. The stacked configuration of the mesofluidic channels 208 allows for increased surface area for the particles of the cell culture fluid 198 to settle, while also allowing the cell culture fluid 198 to have an increased volume to move through, which may allow the device 196 to efficiently process increased volumes of cell culture fluid 198. Thus, the device 196 may sufficiently clarify the cell culture fluid 198 at varying volumes having a high cell density (e.g., >20 million cells/mL). The device 196 may have a capacity of 2,000 L, 4,000 L, or up to 10,000 L.

The mesofluidic channels 208 may range in height 212 from millimeter to centimeter heights, such as between 2 mm and 20 mm (2 cm) in height 212. All of the mesofluidic channels 208 of the device 196 may have the same height 212, or in some embodiments, the mesofluidic channels 208 may vary in height 212 within the millimeter to centimeter range. The mesofluidic channels 208 are each disposed between and fluidically coupled to the fluid inlet manifold 206 and the fluid outlet manifold 210. As such, each mesofluidic channel 208 may be coupled to the fluid inlet manifold 206 at a channel inlet 214 of the mesofluidic channel 208 and coupled to the fluid outlet manifold at a channel outlet 216. The fluid inlet manifold 206 and the fluid outlet manifold 210 may be disposed such that the manifolds 206, 210 are positioned perpendicular to the flow path of the mesofluidic channels 208. The fluid inlet manifold 206 and the fluid outlet manifold 210 may each be sized such that the capacity of the fluid inlet manifold 206 and the capacity of the fluid outlet manifold 210 are greater than the capacity of each mesofluidic channel 208 in order to distribute and collect the cell culture fluid 198 from the mesofluidic channels 208. As such, the device 196 may, in certain embodiments, be devoid of microfluidic features. Consequently, the height 212 of the mesofluidic channels 208 from millimeters up to two centimeters may increase the total capacity of the device 196.

In operation, the cell culture fluid 198 may be provided to the device 196 at a particular flow rate. This is the flow rate that the cell culture fluid 198 passes through the mesofluidic channels 208. The cell culture fluid 198 may enter the fluid inlet manifold 206 and may be distributed substantially evenly between the multiple mesofluidic channels 208. As the cell culture fluid 198 traverses the mesofluidic channels 208, a density difference between the particles contained in the cell culture fluid 198 (e.g., cells) and the surrounding fluid of the cell culture fluid 198 may cause the particles to settle and collect on a lower interior surface 218 of each mesofluidic channel 208. Settling of the particles of the cell culture fluid 198 on the lower interior surface of the mesofluidic channels 208 may be further caused by a separation force 220 acting on the higher density particles within the cell culture fluid 198. The separation force 220 may be an ambient gravitational force, such that no separate or additional force is needed to cause settling of the particles within the mesofluidic channels 208. Settling of the particles of the cell culture fluid 198 within the mesofluidic channels 208 as the cell culture fluid 198 flows through the device 196 may yield a substantially clarified fluid layer 202 (e.g. >80% particle removal) of the cell culture fluid 198 that can be recovered as an output via the fluid outlet 204. As such, a product, such as a protein, of the biopharmaceutical process within the fluid layer 202 of the cell culture fluid 198 may be recovered.

As used herein, the residence time describes the amount of time that it takes for the cell culture fluid 198 to traverse the device 196 from the fluid inlet to the fluid outlet of the device 196, and as such, the amount of time that the cell culture fluid 198 may be within the mesofluidic channels 208 to allow for the particles of the cell culture fluid 198 to sediment. The residence time of the device 196 is defined as the ratio of the total volume of the device 196 to the flow rate of the cell culture fluid 198 through the device 196. The residence time for the device 196 may range from around 10 minutes to 40 minutes or within smaller ranges, such as from 16 minutes to 30 minutes, from 23 minutes to 27 minutes, or any other suitable range or combination of such ranges. This range of residence time of the cell culture fluid 198 within the device 196 allows for settling of the particles to provide a substantially clarified fluid layer 202 within an efficient separation time period (e.g., less than 8 hours processing time for 2,000 L).

Therefore, if a target volume of the cell culture fluid 198 to be processed and a capacity of the device 196 are known, the flow rate of the cell culture fluid 198 can be set or adjusted to provide a target residence time (e.g., 24 minutes, 25 minutes, 26 minutes, and so forth) within the above ranges. The residence time within the above ranges may provide efficient settling of the particles of the cell culture fluid 198, which may be a high cell density cell culture fluid, and clarifying of the fluid layer 202 of the cell culture fluid 198 within a manageable time period, as discussed in greater detail with reference to Tables 4 and 5. As such, the device 196 may be scalable to a target volume to be processed and/or to a particular harvest application.

The particles of the cell culture fluid 198 settle to the lower interior surface 218 as the cell culture fluid 198 traverses the mesofluidic channels 208 due to the density difference between the particles and the fluid of the cell culture fluid and the separation force 220 (e.g., ambient gravitational force). Additionally, the device 196 may be utilized to recover the clarified fluid layer 202 of the cell culture fluid 198. In preferred embodiments, the device 196 does not include any microporous or microfluidic features. Further, the device 196 may be a single use device that may be disposed of after processing of the cell culture fluid 198, as the clarified fluid layer 202 is recovered via the outlet 204 of the device 196.

Figure 3:
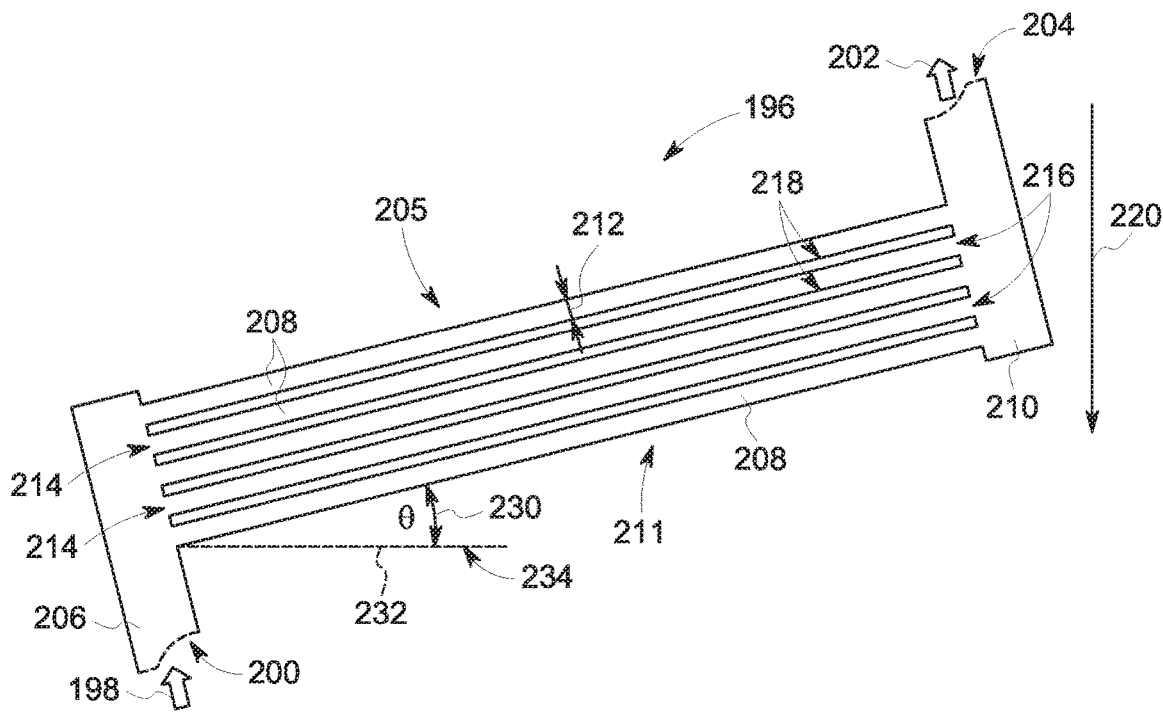
FIG. 3 illustrates a schematic representation of a side view of an embodiment of the separation device of FIG. 2 showing the separation device at an angle, in accordance with aspects of the present disclosure.

FIG. 3 illustrates the separation device 196 positioned at an angle 230 relative to a work surface 232 and to a source 234 of the separation force 220. In some embodiments, during processing of the cell culture fluid 198, the device 196 may be positioned substantially parallel (i.e., non-inclined) to the work surface 232 and the source 234 of the separation force 220, or at a 0° angle or at about a 0° angle (e.g., 0°±5°) relative to the work surface 232, as illustrated in FIG. 2. That is, the work surface 232 may be a surface that is oriented perpendicular to the separation force 234 (e.g., gravitational force). In some embodiments, during processing of the cell culture fluid 198, the device 196 may be positioned at the angle 230 relative to the work surface 232 and the source 234 of the separation force 220, as illustrated in FIG. 3. The angle 232 may position or orient the device such that the channel inlets 214 of the mesofluidic channels 208 are positioned lower than the channel outlets 216.

The device 196 may operate to substantially separate the particles from the fluid layer 202 of the cell culture fluid 198 while not positioned at the angle 230 (e.g., at a 0° angle or about a 0° angle). The density difference between the particles and the fluid layer 202 of the cell culture fluid and the separation force 220 may act to sufficiently separate the particles from the fluid layer 202 even in the absence of an incline. In embodiments where the device 196 is positioned at the angle 230, the angle 230 may provide the benefit of helping to evacuate air from the device 196 and not as a force for operation of the device 196.

The angle 230 may be an angle between substantially 0°-30°, or an angle between substantially 0°-10°, such as 10°, 5°, or about 0° (e.g., 0°±5°). As such the separation device 196 may be referenced herein as a non-inclined settler. In contrast, inclined settlers are dependent upon the Boycott effect, which may require operation angles around 30° or greater to achieve sedimentation. In some embodiments, the device 196 may be positioned at the angle 230 throughout the separation process. However, in some embodiments, the device 196 may be intermittently or periodically tilted to the angle 230 to evacuate air from the mesofluidic channels 208 to increase separation efficiency of the device 196.

FIGS. 4A-4H illustrate embodiments of different configurations of the fluid inlet(s) 200, the fluid inlet manifold(s) 206, the fluid outlet manifold(s) 210, and the fluid outlet(s) 204 of the device 196. In certain configurations of the device 196, the device 196 may include one or more fluid inlets 200 and one or more fluid outlets 204 (e.g., 1, 2, 3). Additionally, the device 196 may include one or more of the fluid inlet manifold 206 to couple the fluid inlet(s) 200 to the channel inlets 214, one or more of the fluid outlet manifold 210 to couple the fluid outlet(s) 204 to the channel outlets 216, or both the fluid inlet manifold(s) 206 and the fluid outlet manifold(s) 210. Further, in some configurations, the device 196 may include one or more lateral inlet channels 236 that may distribute the cell culture fluid from the one or more fluid inlet manifolds 206 between the channel inlets 214 and/or one or more lateral outlet channels 238 that may collect the clarified fluid layer 202 from the channel outlets 216 and distribute the clarified fluid layer 202 to the one or more fluid outlet manifolds 210.

Figure 4A:
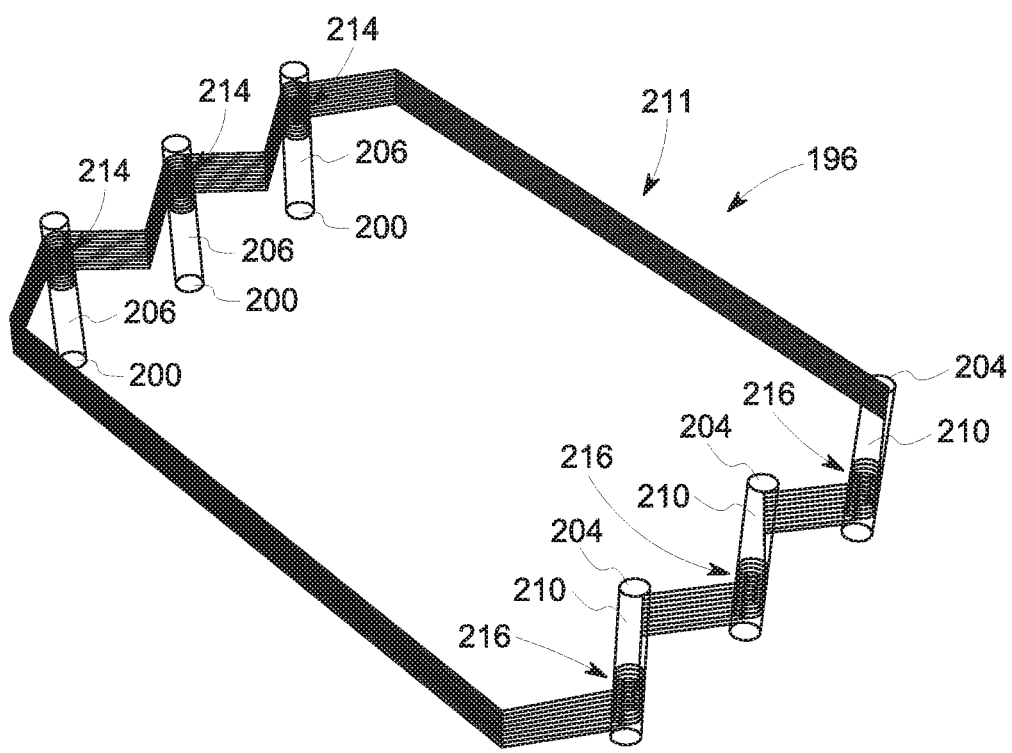
FIG. 4A illustrates a schematic cut away representation of a perspective view of an embodiment of the separation device of FIG. 2 showing an inlet and outlet configuration, in accordance with aspects of the present disclosure.

FIG. 4A illustrates a configuration of the device 196 having multiple of the fluid inlet manifolds 206, each coupling one of the fluid inlets 200 to the one or more channel inlets 214 of the mesofluidic channels 208 of the separation portion 211. The cell culture fluid 198 flowed into the multiple fluid inlets 200 is distributed between the one or more channel inlets 214 via the multiple fluid inlet manifolds 206. Additionally, the device 196 includes multiple of the fluid outlet manifolds 210, each coupled to the one or more channel outlets 216 of the mesofluidic channels 208. The clarified fluid layer 202 produced as the cells and/or other particles fall out of the cell culture fluid 198 as it is flowed through the device 196 exit the mesofluidic channels 208 via the multiple fluid outlet manifolds 210 and exit the device 196 via the respective fluid outlets 204. Multiple fluid inlets 200 and fluid outlets 204 may allow for an increased flow rate of the cell culture fluid 198 through the device, thus increasing the volume of cell culture fluid 198 that the device 196 may efficiently process within a particular time period.

Figure 4B:
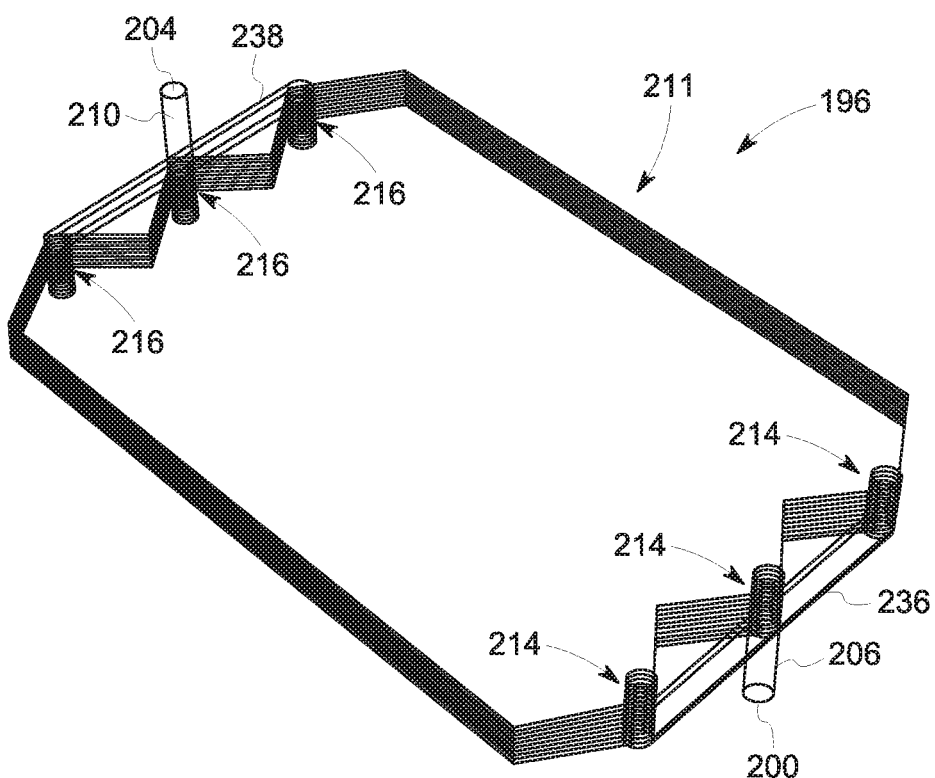
FIG. 4B illustrates a schematic cut away representation of a perspective view of an embodiment of the separation device of FIG. 4A showing another inlet and outlet configuration, in accordance with aspects of the present disclosure.

FIG. 4B illustrates a configuration of the device 196 having a single fluid inlet 200 coupled to a single fluid inlet manifold 206, as well as a single fluid outlet 204 coupled to a single fluid outlet manifold 210. Additionally, the fluid inlet manifold 206 is coupled to one or more lateral inlet channel 236. The lateral inlet channel 236 may be disposed perpendicular to the fluid inlet manifold 206 such that the cell culture fluid 198 that is flowed into the fluid inlet manifold 206 is distributed to each of the channel inlets 214 via the lateral inlet channel 236. Further, the channel outlets 216 are coupled to the fluid outlet manifold 210 via the lateral outlet channel 238. The lateral outlet channel 238 may be disposed perpendicular to the mesofluidic channels 208 such that the clarified fluid layer 202 from each channel outlet 216 is collected in the lateral outlet channel 238 and distributed to the single fluid outlet manifold 210 to exit the device 196. Inclusion of the lateral inlet channel 236 and/or the lateral outlet channel 238 may provide for minimization of the profile of the device 196 while still allowing for substantially equal distribution of the cell culture fluid 198 at a particular flow rate through the device 196.

Figure 4C:
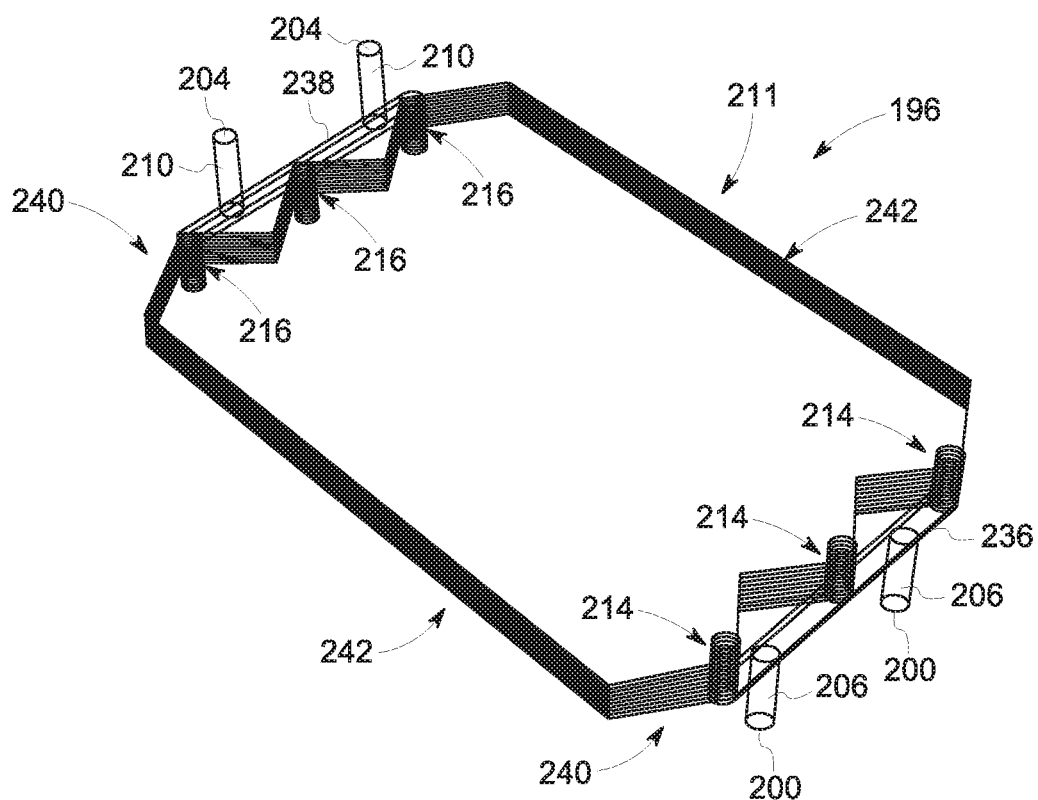
FIG. 4C illustrates a schematic cut away representation of a perspective view of an embodiment of the separation device of FIG. 4A showing another inlet and outlet configuration, in accordance with aspects of the present disclosure.

FIG. 4C illustrates a configuration of the device 196 having multiple fluid inlet manifolds 206 and fluid outlet manifolds 210 coupled to the lateral inlet channel 236 and the lateral outlet channel 238, respectively. As with the configuration shown in FIG. 4B, the lateral inlet channel 236 may be disposed perpendicular to the fluid inlet manifold 206 such that the cell culture fluid 198 that is flowed into the fluid inlet manifold 206 is distributed to each of the channel inlets 214 via the lateral inlet channel 236. Additionally, the lateral outlet channel 238 may be disposed perpendicular to the mesofluidic channels 208 such that the clarified fluid layer 202 from each channel outlet 216 is collected in the lateral outlet channel 238 and distributed to the single fluid outlet manifold 210 to exit the device 196. In some configurations, such as the configuration shown in FIG. 4C, the fluid inlet manifold(s) 206 may be disposed directly across from, or in line with, the fluid outlet manifold(s) 210 on opposite ends 240 of the device 196.

Figure 4D:
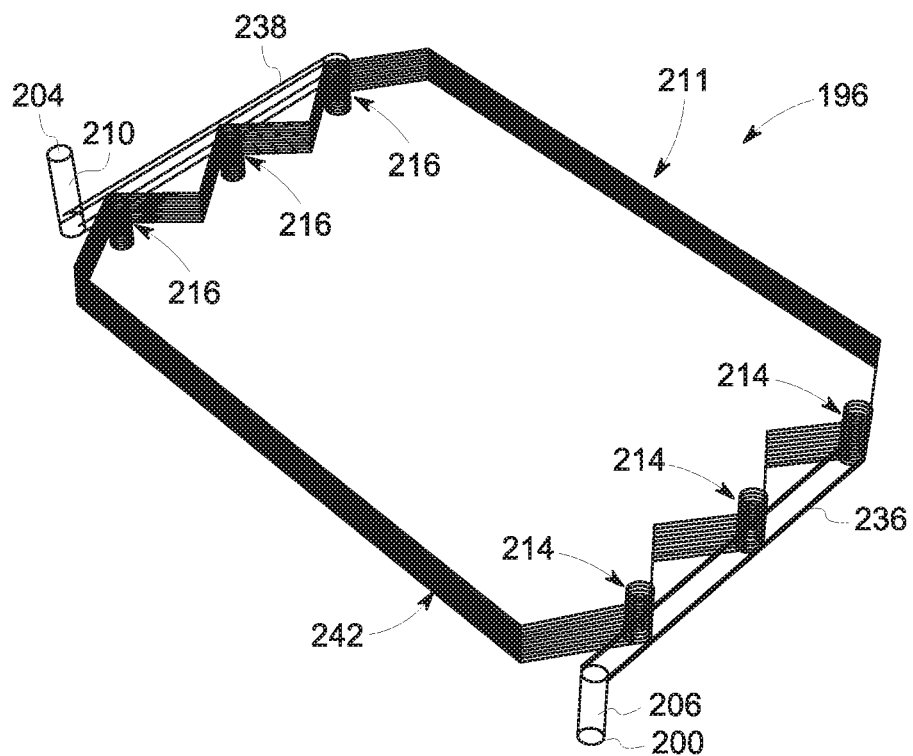
FIG. 4D illustrates a schematic cut away representation of a perspective view of an embodiment of the separation device of FIG. 4A showing another inlet and outlet configuration, in accordance with aspects of the present disclosure.

FIG. 4D illustrates a configuration of the device 196 having a single fluid inlet manifold 206 and a single fluid outlet manifold 210 coupled to the lateral inlet channel 236 and the lateral outlet channel 238, respectively. The configuration shown in FIG. 4D is similar to that shown in 4B, except for the position of the fluid inlet manifold 206 and the fluid outlet manifold 210 about the ends 240 relative to a side 242 of the device 196. While both FIGS. 4B and 4D show configurations where the fluid inlet manifold 206 and the fluid outlet manifold 210 are disposed directly across from each other on the opposite ends 240 of the device, FIG. 4D shows the fluid inlet manifold 206 and the fluid outlet manifold 210 disposed adjacent to one of the sides 242 rather than disposed at a center position between the sides 242 of the device, as shown in FIG. 4B.

Figure 4E:
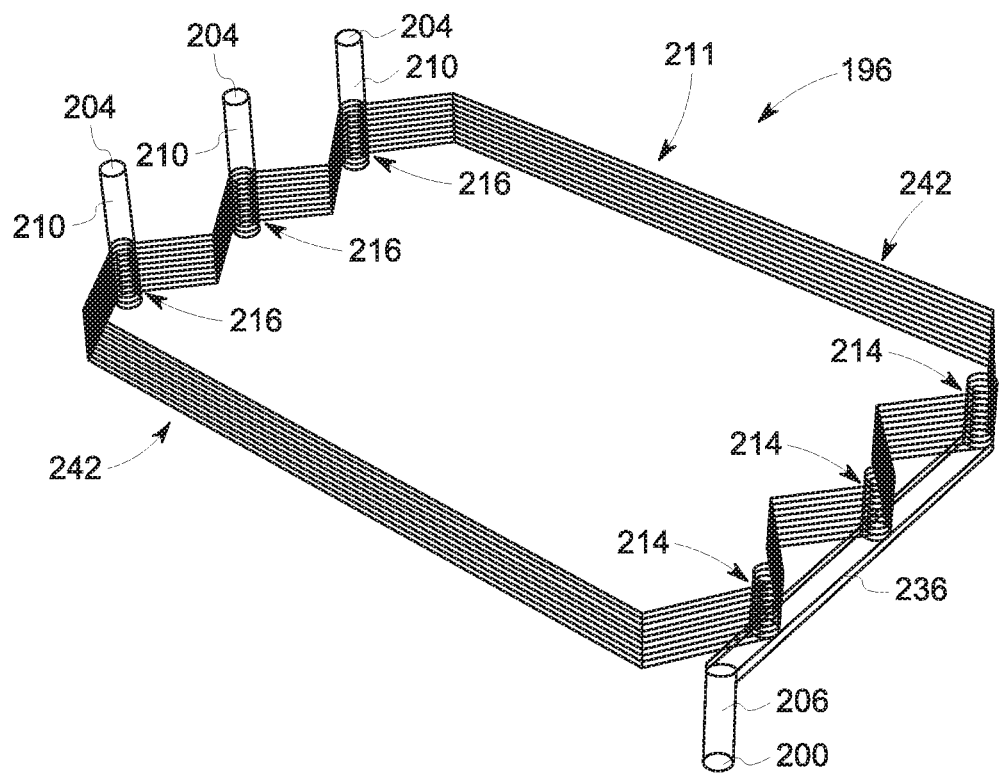
FIG. 4E illustrates a schematic cut away representation of a perspective view of an embodiment of the separation device of FIG. 4A showing another inlet and outlet configuration, in accordance with aspects of the present disclosure.
Figure 4F:
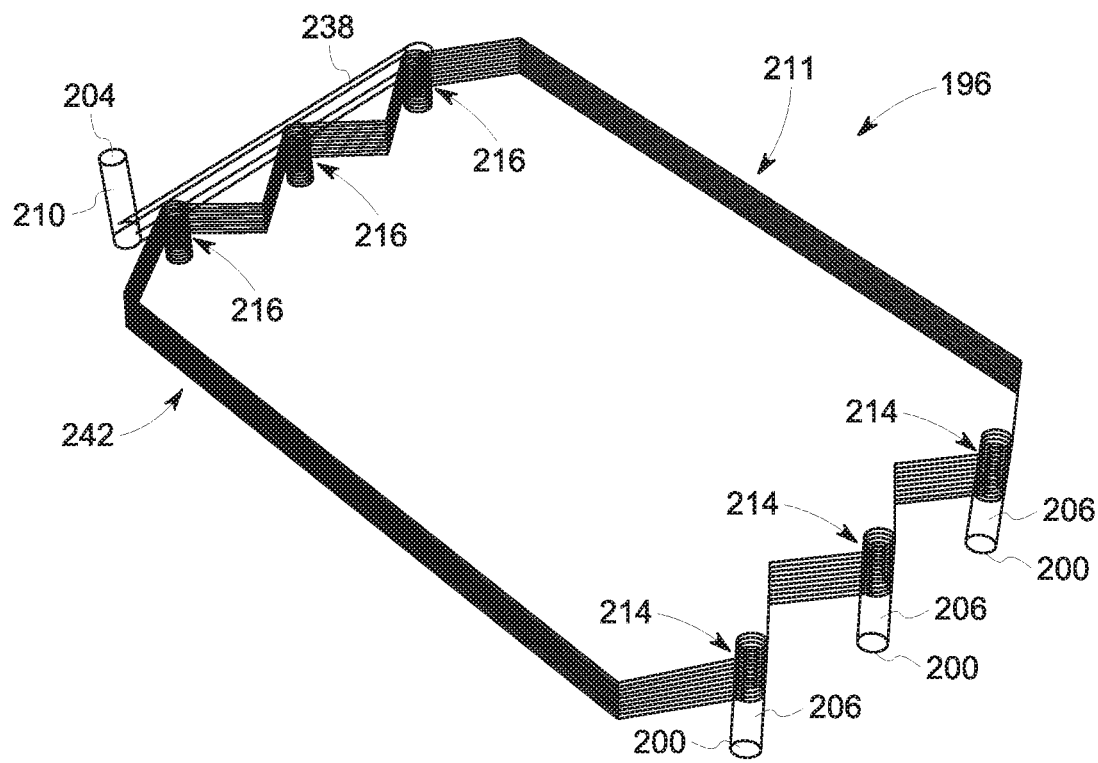
FIG. 4F illustrates a schematic cut away representation of a perspective view of an embodiment of the separation device of FIG. 4A showing another inlet and outlet configuration, in accordance with aspects of the present disclosure.

FIG. 4E illustrates a configuration of the device 196 having a single fluid inlet 200 and fluid inlet manifold 206, which is coupled to the channel inlets 214 via the lateral inlet channel 236. Additionally, the device 196 includes multiple fluid outlets 204 each coupled to the one or more channel outlets 216 via a respective one of multiple fluid outlet manifolds 210. In an opposite configuration, FIG. 4F illustrates a configuration of the device 196 having multiple fluid inlets 200 each coupled to the one or more channel inlets 214 via a respective one of multiple fluid inlet manifolds 206. Additionally, the device 196 shown in FIG. 4F includes a single fluid outlet 204 and fluid outlet manifold 210 coupled to the one or more channel outlets via the lateral outlet channel 238. In both configurations, the single fluid inlet manifold 206 shown in FIG. 4E and the single fluid outlet manifold 210 shown in FIG. 4F are each disposed adjacent to a side 242 of the device 196, rather than at a center position between each side 242 of the device 196. Further, as shown in both configurations of FIGS. 4E and 4F, when multiple fluid inlet manifolds 206 and/or multiple fluid outlet manifolds 210 are present, they may be disposed equally spaced between the sides 242 of the device 196.

Figure 4G:
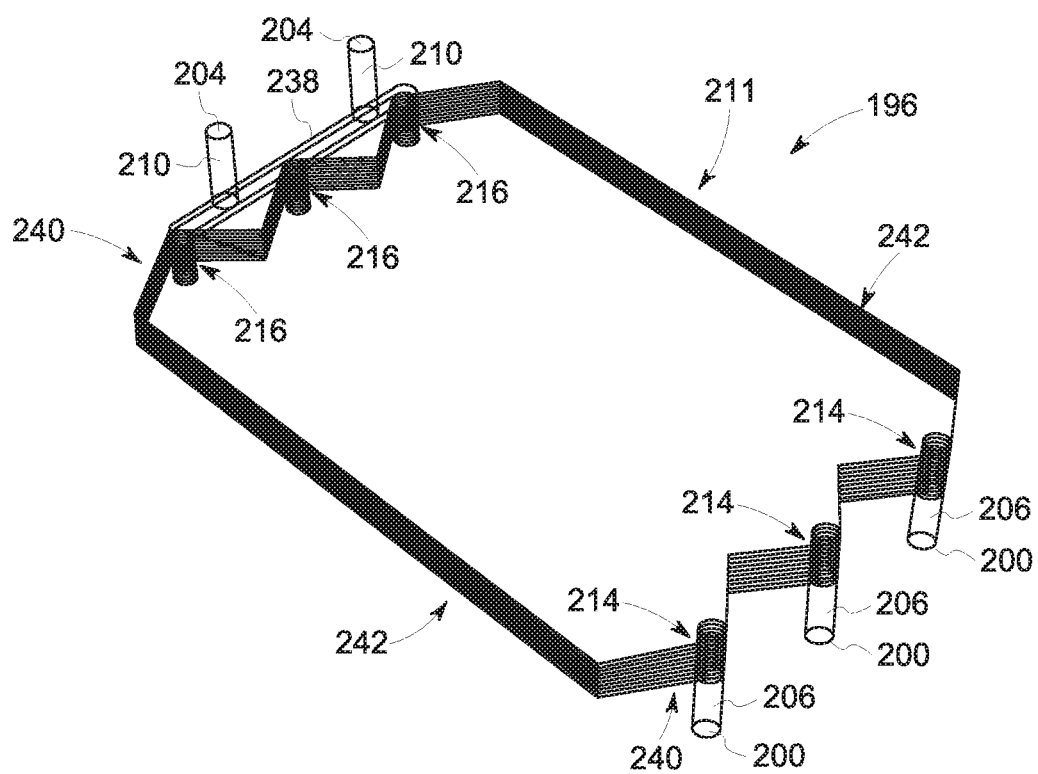
FIG. 4G illustrates a schematic cut away representation of a perspective view of an embodiment of the separation device of FIG. 4A showing another inlet and outlet configuration, in accordance with aspects of the present disclosure.

FIG. 4G illustrates a configuration of the device 196 having multiple fluid inlets 200 each coupled to the one or more channel inlets 214 of the device 196 via a respective one of multiple fluid inlet manifolds 206. Additionally, the device 196 of FIG. 4G includes multiple fluid outlets 204 and fluid outlet manifolds 210 coupled to the one or more channel outlets 216 via the lateral outlet channel 238. While there are multiple fluid inlet manifolds 206 and multiple fluid outlet manifolds 210, the amount of each present on the device 196 does not correspond. For example, the device 196 of FIG. 4G includes three fluid inlet manifolds 206 and only two fluid outlet manifolds 210. In such configurations, the fluid inlet manifolds 206 and the fluid outlet manifolds 210 may each be equally spaced between the sides 242 of the device 196, however the fluid outlet manifolds 210 may not be disposed directly across from the fluid inlet manifolds 206 on respective ends 240 of the device 196.

Figure 4H:
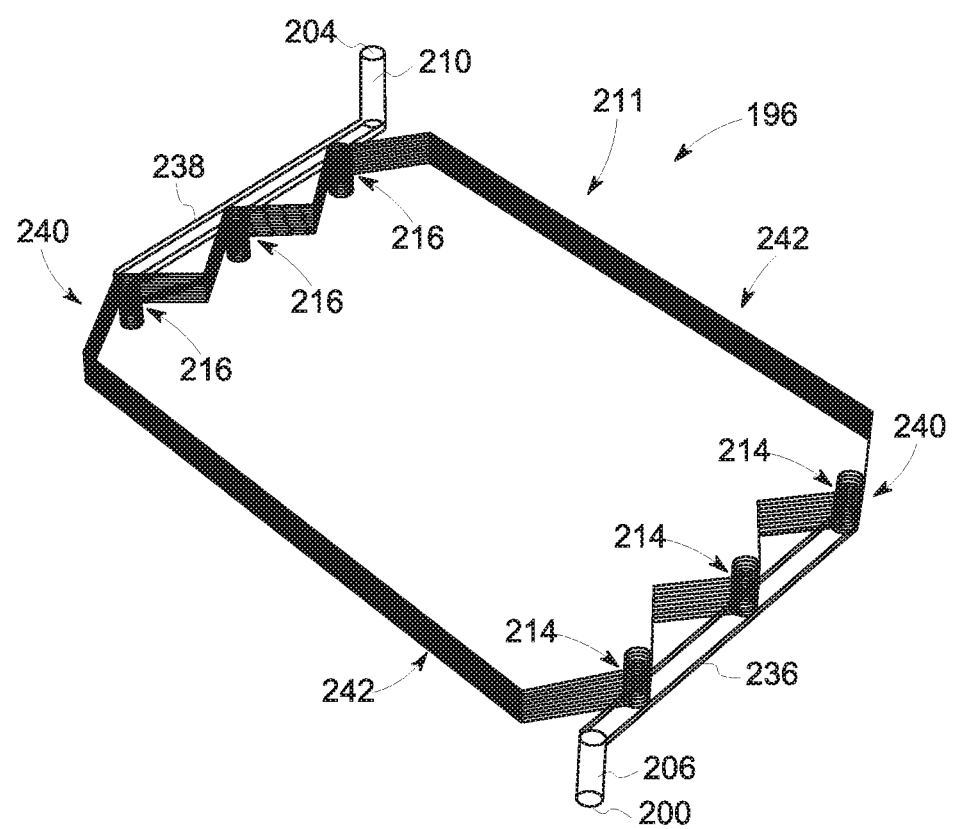
FIG. 4H illustrates a schematic cut away representation of a perspective view of an embodiment of the separation device of FIG. 4A showing another inlet and outlet configuration, in accordance with aspects of the present disclosure.

FIG. 4H illustrates a configuration of the device 196 having a single fluid inlet 200 and a respective single fluid inlet manifold 206, as well as a single fluid outlet 204 and a respective single fluid outlet manifold 210. Additionally, the fluid inlet manifold 206 is coupled to the one or more channel inlets 214 via the lateral inlet channel 236 and the fluid outlet manifold 210 is coupled to the one or more channel outlets 216 via the lateral outlet channel 238. In the configuration shown in FIG. 4H, the fluid inlet manifold 206 is positioned along an end 240 adjacent to one side 242 of the device 196. The fluid outlet manifold 210 is positioned along an opposite end 240 adjacent to an opposite side 242 of the device 196, such that the fluid inlet manifold 206 and the fluid outlet manifold 210 are not disposed directly across from each other.

The alternative configurations of the device 196 shown in FIGS. 4A-4H illustrate non-limiting examples of the device 196 and are not meant to illustrate all possible configurations. The device 196 may include any suitable quantity of fluid inlets 200, fluid inlet manifolds 200, fluid outlets 204, fluid outlet manifolds 210, and may or may not include the lateral inlet channel 236 and/or the lateral outlet channel 238. Varying amounts of fluid inlets 200 and fluid outlets 204, as well as of the fluid inlet manifolds 206 and the fluid outlet manifolds 210, may allow customization or selection of a pressure drop across the device 196, and thus, may vary the flow rate of the cell culture fluid 198 through the device 196. This may allow for customization of the device 196 based on a target application. The fluidic path between the fluid inlet 200 and the fluid outlet 204 of the device 196 may be unidirectional in a linear or serpentine configuration. Additionally, inclusion of the lateral inlet channel 236 and/or the lateral outlet channel 238 may provide for minimization of the profile of the device 196 while still allowing for substantially equal distribution of the cell culture fluid 198 at a particular flow rate through the device 196.

Figure 5:
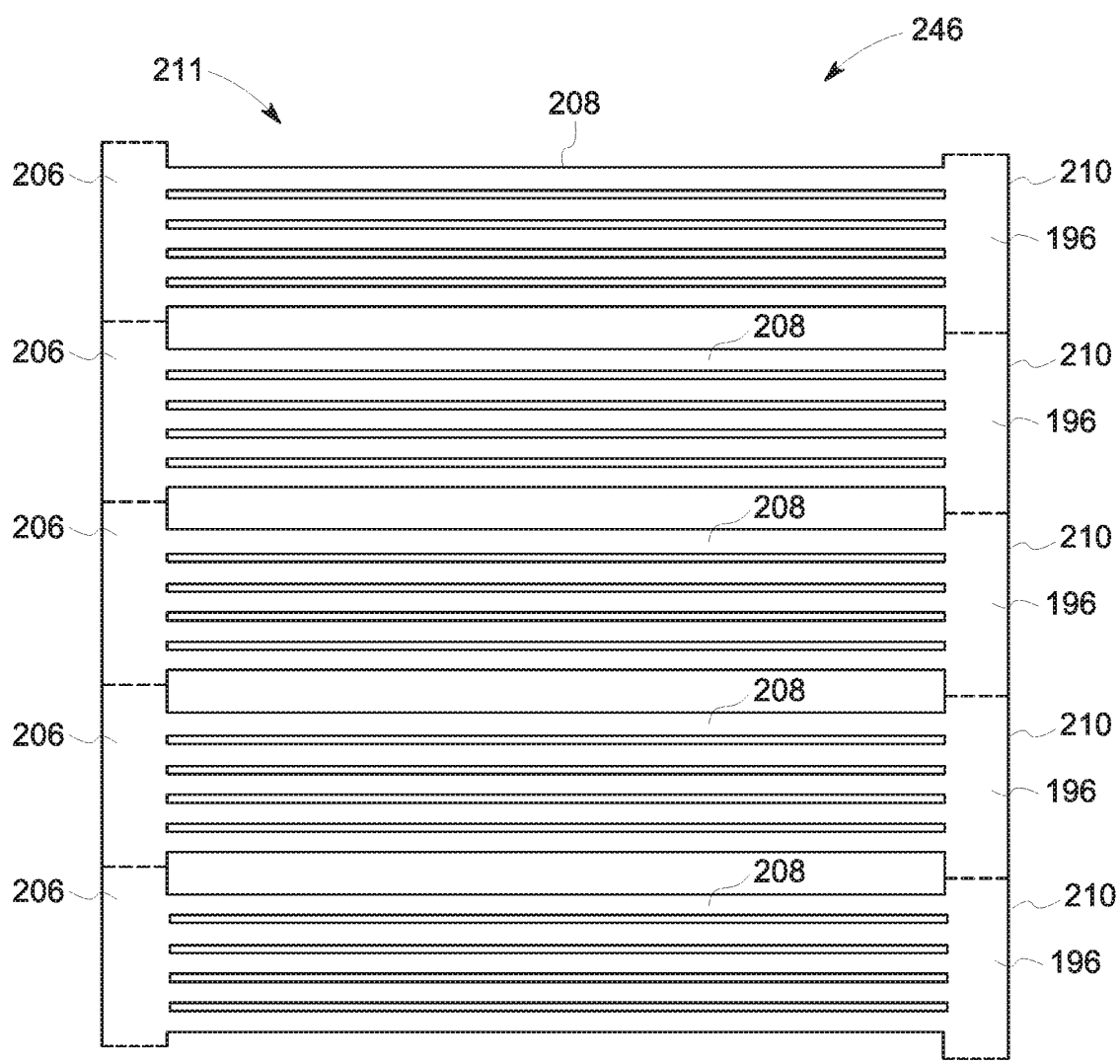
FIG. 5 illustrates a schematic representation of a side view of an embodiment of a modular separation device including multiple of the separation devices of FIG. 2, in accordance with aspects of the present disclosure.

FIG. 5 illustrates an embodiment of a modular separation device 246 including two or more of the separation devices 196 as modular subunits. In the illustrated embodiment, the one or more fluid inlet manifolds 206 and the one or more fluid outlet manifolds 210 of each device 196 may be coupled, respectively, such that a length of the fluid inlet manifold 206 and the fluid outlet manifold 210 is increased forming the fluid inlet manifold 206 and the fluid outlet manifold 210 for the modular separation device 246. As each device 196 includes one or more mesofluidic channels 208 coupled between the fluid inlet manifold 206 and the fluid outlet manifold 210, the modular separation device 246 will include an increased number of the mesofluidic channels 208 as additional device 196 are added.

Use of the devices 196 as modular subunits may provide the modular separation device 246 with the particular capacity to allow for efficient processing of the volume of a target cell culture fluid 198. In some embodiments, the devices 196 (e.g., modular subunits) may allow for increasing or decreasing the number of mesofluidic channels 208, varying the position and/or amount of the fluid inlet(s) 200 and/or the fluid outlet(s) 204, varying the presence or absence of the fluid inlet manifold 206 and/or the fluid outlet manifold 210, or any combination thereof. Modularity of the modular separation device 246 using the devices 196 may allow for use of the devices 196 based on a target application.

Figure 6:
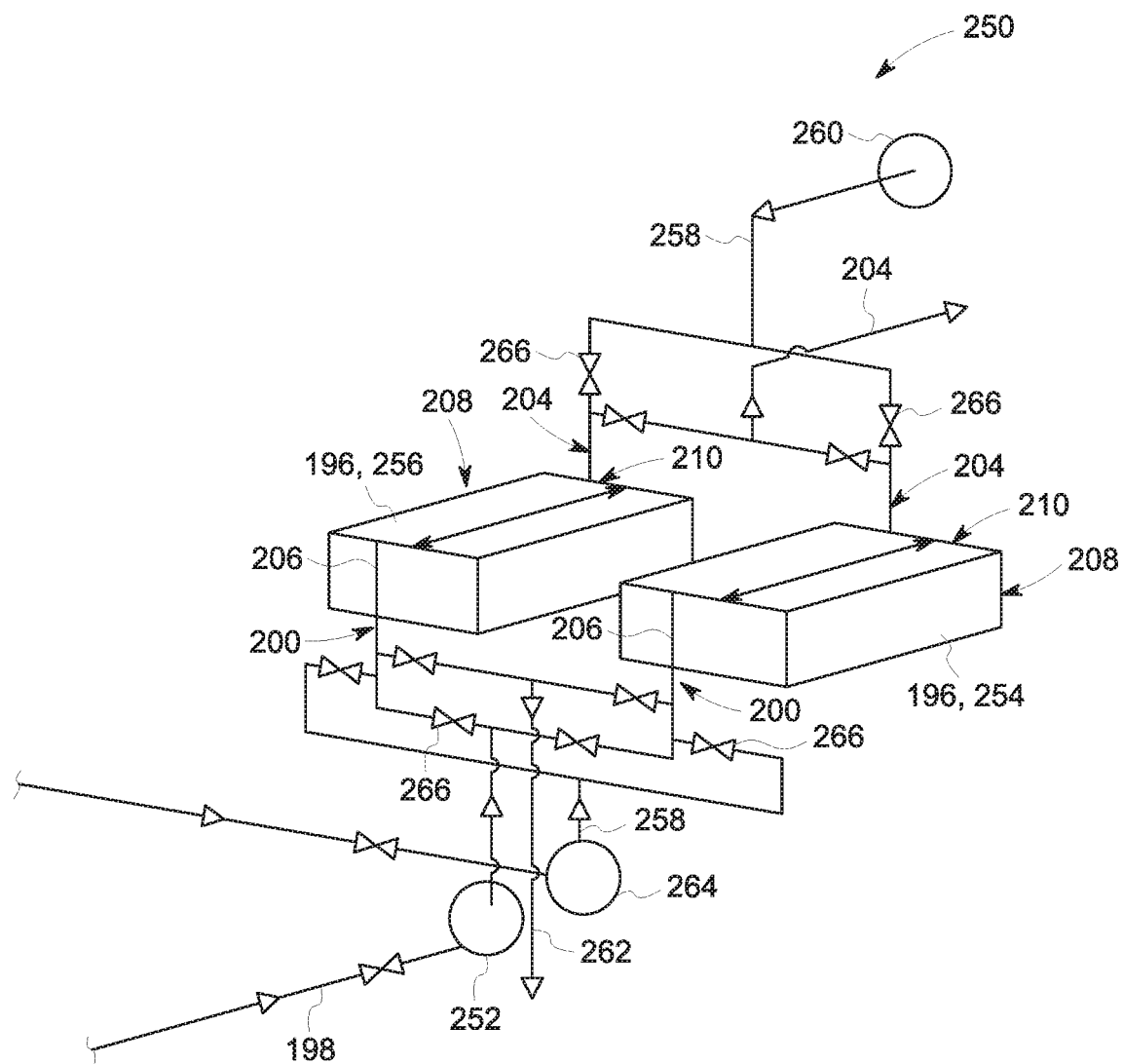
FIG. 6 illustrates a schematic representation of an embodiment of alternating bioprocessing system including multiple of the separation devices of FIG. 2, in accordance with aspects of the present disclosure.

In some embodiments, the devices 196, including a device 296 discussed below with reference to FIGS. 8-12, and the modular separation devices 246 can be operated in an alternating arrangement, where one or more device is fluidically coupled to the cell culture fluid to produce a substantially clarified product, while an additional one or more devices are fluidically coupled to recover the cells and/or other particulates to the reactor or separate container. Such a process allows for semicontinuous or continuous processing of cell culture fluid while recovering the cells and/or other particulates. Additionally, such an arrangement may allow for increased system processing capacity. As such, FIG. 6 illustrates an alternating bioprocess system 250 having two of the devices 196 arranged for operation in parallel. Although discussed in terms of two of the device 196, it should be understood that the alternating bioprocess system 250 may be applicable to more than two devices 196 and/or may include the modular separation devices 246.

In the alternating bioprocess system 250, the devices 196 may be arranged in a parallel operational configuration, each fluidically coupled by the respective fluid inlet 200 the bioreactor 182 or other source of the cell culture fluid 198. In some embodiments, an inlet pump 252 may be used to pump the cell culture fluid 198 to the fluid inlets 200 of the device 196. In operation, the cell culture fluid may be flowed through a first device 254 of the devices 196, while flow is blocked to a second device 256 of the devices 196. The cell culture fluid may be flowed through the mesofluidic channels 208 of the first device 254, within which the cells and/or other particulates may sediment out of the cell culture fluid. Before the terminal capacity of the first device 254 is reached, the flow of the cell culture fluid from the bioreactor may be routed to the second device 256 and blocked from flowing into the first device 254.

In some embodiments, if the cells and/or other particulates that sediment out of the cell culture fluid are an intended product of the bioprocess, the first device 254 may be washed of the settled cells and/or particulates using the same fluid or an alternate compatible fluid 258, such as a buffer or purge air. The fluid of the retained cells and/or other particulates may be exchanged with the same or alternate compatible fluid 258 using a common or separate fluidic conduit fluidically coupled to the outlet of the first device 254, such that flow is reversed using the same or alternate compatible fluid within the device 254 from the fluid outlet 204 to the fluid inlet 200 of the first device 245. In some embodiments, the alternating bioprocess system 250 may include a purge pump 260 may be used to create the reverse flow of the alternate compatible fluid 258 into the fluid outlet 204 of the first device 254. The reverse flow may return the cells and/or other particulates retained within the first device 254 (e.g., retentate) to the bioreactor 182 and/or a separate sterile container fluidically coupled to the device 196 and/or the bioreactor 182 via collection line 262. The first device 254 may then be ready to be used for additional separation. In some embodiments, the first device 254 may be washed by flowing the alternate compatible fluid 258 (e.g., buffer) through the first device 254 using a common or separate fluidic conduit fluidically coupled to the fluid inlet 200 of the first device 254. A buffer pump 264 may be used to flow the alternate compatible fluid 258 through the first device 254.

The cell culture fluid from the bioreactor 182 may be flowed through the second device 256 while the cells and/or other particulates retained within the first device 254 are removed. Before the terminal capacity of the second device 256 is reached, the flow of the cell culture fluid from the bioreactor may be routed to the first device 254 and blocked from flowing into the second device 256. As such, the second device 256 may then be washed of the retained cells and/or other particulates. Multiple valves 266 may be used throughout the alternating bioprocess system 250 to control the flow of the cell culture fluid, the clarified fluid, and the alternate compatible fluid. Thus, the first and second devices 254, 256 may be used in an alternating arrangement to increase efficiency and separation capacity by allowing for semicontinuous or continuous processing of the cell culture fluid.

Figure 7:
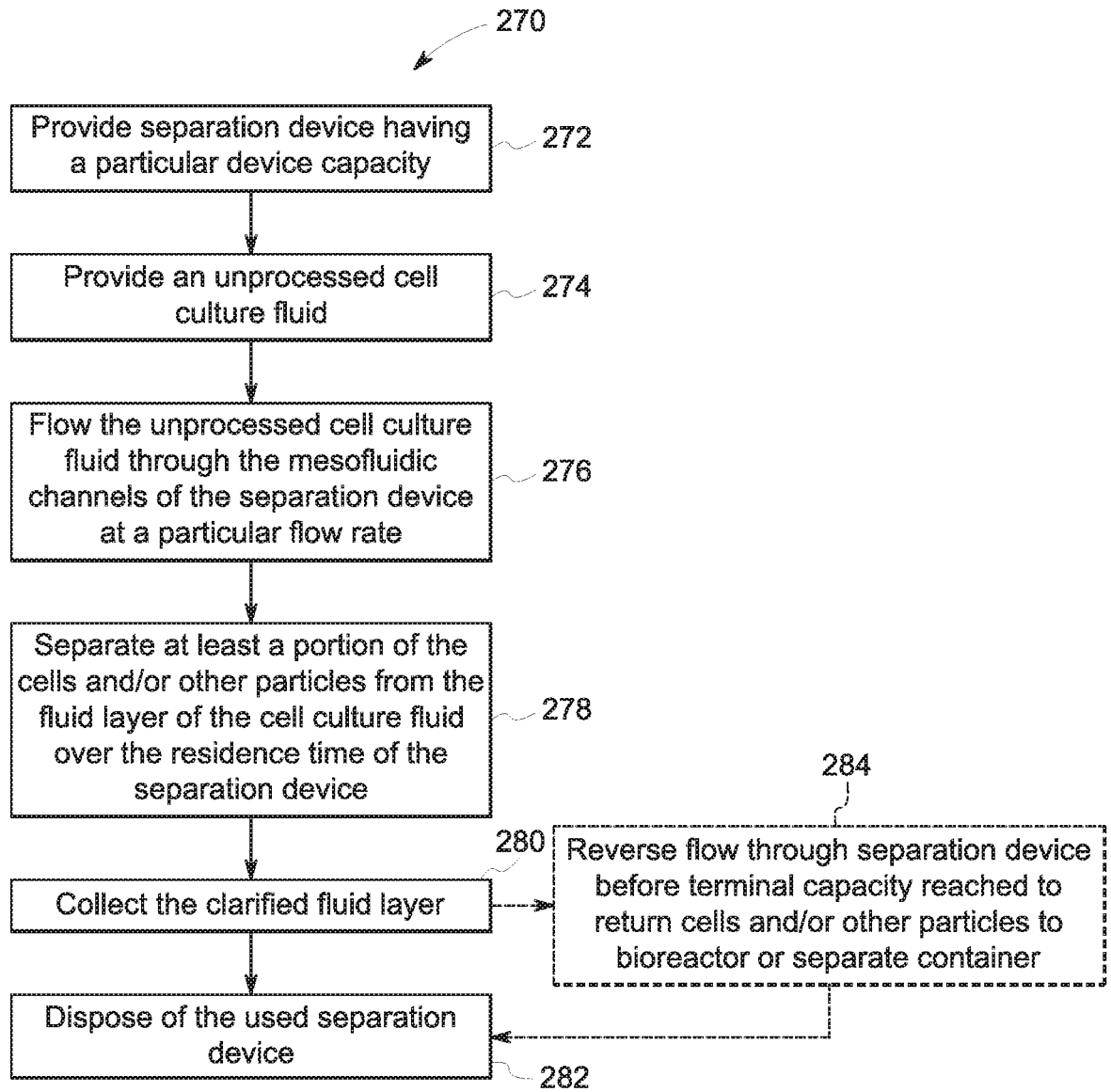
FIG. 7 is a flow chart of an embodiment of a method for separating particles from a fluid utilizing the separation device of FIG. 2, in accordance with aspects of the present disclosure.

FIG. 7 is a flow chart of an embodiment of a method 270 of clarifying the cell culture fluid 198 using the device 196. Because of the single use, disposable nature of the device 196, which may have a capacity of 2,000 L, 4,000 L, or up to 10,000 L, in some embodiments, the device 196 may be sterilized (e.g., gamma sterilized) and/or packaged prior to use. At step 272, the device 196 may be provided having a particular capacity to allow for efficient processing of a target cell culture fluid 198 volume. As previously discussed, the device 196 may include multiple mesofluidic channels 208 regularly stacked and arranged between the fluid inlet manifold 206 and the fluid outlet manifold 210. The quantity and size (e.g., height) of the mesofluidic channels 208 may account for the particular capacity of the device 196. In some embodiments, the device 196 may be modular such that it includes modular subunits. In such embodiments, the modular subunits may be used to provide the device 196 with the particular capacity to allow for efficient processing of the target cell culture fluid 198 volume. In some embodiments, the modular subunits may allow for increasing or decreasing the number of mesofluidic channels, varying the position and/or amount of the fluid inlet(s) 200 and/or the fluid outlet(s) 204, varying the presence or absence of the fluid inlet manifold 206 and/or the fluid outlet manifold 210, or any combination thereof. In some embodiments, the device 196 may be provided at a substantially 0° angle 230 (e.g., 0°±5°) relative to the work surface 232 and the source 234 of the separation force 220. However, in some embodiments, the device 196 may be provided at an angle 230 within a range of 1°-29° or between 1°-10°. The angle 230 may not be necessary for operation of the device, for example to create a separation force, but may only be used to evacuate air from the device 196.

Next, at step 274, the unprocessed cell culture fluid 198 may be provided from a source, such as a bioreactor, as a cell suspension containing particles (e.g., cells) suspended in the fluid layer 202. The unprocessed cell culture fluid 198 may contain any density of particles, including a high density of particles, such as within a cell density range of 1-200 million particles/mL (e.g., cells/mL). In some embodiments, additional particles may be added to the cell culture fluid 198 to aid in improving settling performance of the device 196. For example, a flocculant, such as poly(diallyldimethylammonium chloride (PDADMC), may be added to the cell culture fluid 198. The flocculant may aggregate the particles, as well as other debris in the cell culture fluid 198, into larger particles, which may settle faster based on the density difference between the larger particles and the fluid of the cell culture fluid 198. This in turn may improve separation performance of the device 196, especially at higher particle densities (e.g., cell densities). In some embodiments, the particles may be recovered from the device 196. In such embodiments, a charge of the added flocculant may also be used to capture charged species in the cell culture fluid 198, such as DNA. In some embodiments, ion exchange or affinity beads may be added to the cell culture fluid 198 to capture a product or protein to be recovered. The beads may settle within the device 198 and the beads and the product may be recovered from the device. Therefore, in some embodiments, the device 198 may include a port for recovering the settled particles.

Next, at step 276, the unprocessed cell culture fluid 198 may be flowed through the mesofluidic channels 208 of the device 198 at a particular flow rate. The particular flow rate at which the cell culture fluid 198 is flowed through the device 198 may be determined based on the capacity of the device 198 in order to provide a residence time (e.g. ratio of device capacity to the flow rate) within the above described range to increase performance and efficiency of the device 198. Next, at step 278, at least a portion of the particles within the cell culture fluid 198 may be separated from the fluid layer 202 of the cell culture fluid 198 over the residence time as the cell culture fluid 198 flows through the mesofluidic channels 208 of the device 198. As previously discussed, the particles may settle to the lower interior surface 218 of the mesofluidic channels due to a density difference between the particles and the fluid layer 220 of the cell culture fluid 198 and the separation force 220. In some embodiments, the separation force 220 may be an ambient gravitational force. The device 196 may allow for separation and retention within the device 196 of up to approximately 90%-99.9% of the particles within the cell culture fluid 198.

Next, at step 280, the stream of the fluid layer 202 substantially devoid of the particles may be collected via the fluid outlet 204 of the device. The collected clarified fluid layer 202 may contain the target product of harvest process. Next, at step 282, if the target product is collected in the clarified fluid layer 202, the device 196 may be discarded, as the device 196 may be a single use, disposable separation device. Therefore, the device 196 may provide a single use, disposable separation device that may allow for efficient clarification of a cell culture fluid containing a wide particle density range. Additionally or alternatively, in some embodiments, as previously discussed, the flow through the separation device 196 may be reversed before a terminal capacity of the device 196 is reached, at step 284. Reversing the flow through the device 196 may allow for return of the cells and/or other particles that fell out of the cell culture fluid 198 as it was flowed through the device 196 to the bioreactor or to a separate container for recovery. While the method 250 is described for use of the device 196, it should be understood that the method 250 may also be used for the embodiments of the separation device discussed below with regard to FIGS. 8-12.

Figure 8:
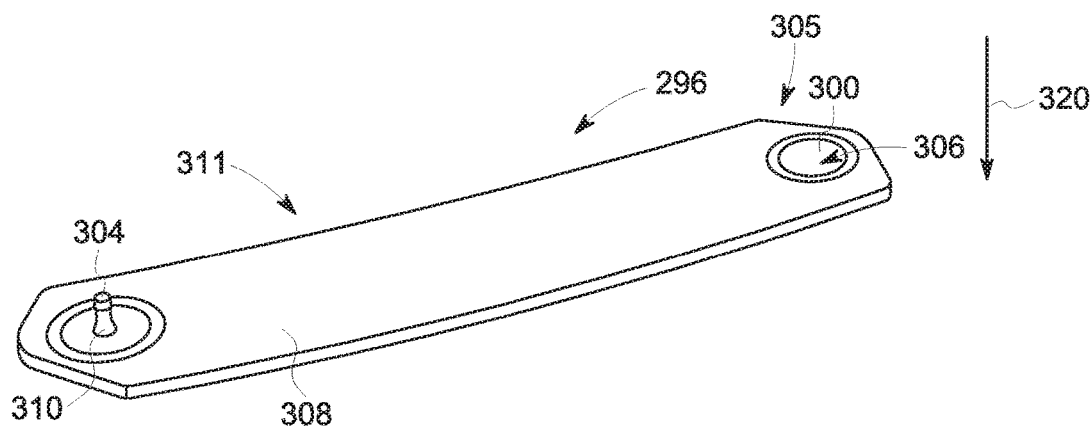
FIG. 8 illustrates a schematic representation of a perspective view of an additional embodiment of a separation device of FIG. 1, in accordance with aspects of the present disclosure.

FIG. 8 illustrates an embodiment of a separation device 296 made from a flexible material, (preferably fabricated with a gamma compatible polymer) such that the separation device 296 forms a bag configuration having one or more channels for separation of cells and/or other particles from the cell culture fluid 198. The device 296 may be a single-use device that may be discarded after use for separation. The device 296 may receive an input of a cell culture fluid 198 (e.g., the unclarified solution containing cells and/or other particles suspended in a base fluid) via a fluid inlet 300. The device 296 may receive the cell culture fluid 198 from the bioreactor 182, or other source, at a particular flow rate. A body 305 of the device 296 may include one or more fluid inlet manifolds 306, one or more mesofluidic channels 308 (e.g., channels having heights within the millimeter to centimeter range), and one or more fluid outlet manifolds 310. The fluid inlet manifold 306 may couple the fluid inlet 300 to the one or more mesofluidic channels 308. The device 296 may include any number of mesofluidic channels 308 (e.g., 1, 2, 3, 4, 5, 6, etc.) arranged in a stacked or parallel configuration providing a series of stacked mesofluidic channels in a separation portion 311 of the body 305 of the device 296.

The one or more mesofluidic channels 308 may each range in height from millimeter to centimeter heights, such as between 2 mm and 20 mm (2 cm) in height. The one or more mesofluidic channels 308 are each disposed between and fluidically coupled to the fluid inlet manifold 306 and the fluid outlet manifold 310. The fluid inlet manifold 306 and the fluid outlet manifold 310 may be disposed such that the manifolds 306, 310 are positioned perpendicular to the flow path of the one or more mesofluidic channels 308. The structure of the device 296, including the fluid inlet manifold 306 and the fluid outlet manifold 310, may be formed from perimeter-bonded flexible plastic or polymer layers, as discussed in greater detail with respect to FIGS. 9-11.

Similar to the device 196 discussed above, in operation, the cell culture fluid 198 may be provided to the device 296 at a particular flow rate. This is the flow rate that the cell culture fluid 198 passes through the mesofluidic channels 308. The cell culture fluid 198 may enter the fluid inlet manifold 306 and may be distributed substantially evenly between the one or more mesofluidic channels 308. As the cell culture fluid 198 traverses the one or more mesofluidic channels 308, a density difference between the cells and/or other particles contained in the cell culture fluid 198 (e.g., cells) and the surrounding fluid of the cell culture fluid 198 may cause the cells and/or other particles to settle and collect on a lower interior surface of each mesofluidic channel 308.

Settling of the cells and/or other particles of the cell culture fluid 198 within the one or more mesofluidic channels 308 may be further caused by the separation force 320 acting on the higher density particles within the cell culture fluid 198. The separation force 320 may be an ambient gravitational force, such that no separate or additional force is needed to cause settling of the cells and/or other particles within the one or more mesofluidic channels 308. Settling of the particles of the cell culture fluid 198 within the mesofluidic channels 308 as the cell culture fluid 198 flows through the device 196 may yield the substantially clarified fluid layer 202 (e.g., substantially cell and/or particle free fluid layer) of the cell culture fluid 198 that can be recovered as an output via the fluid outlet 304. As such, a product, such as a protein, of the biopharmaceutical process within the fluid layer 202 of the cell culture fluid 198 may be recovered.

As noted above, the residence time of the device 296, as used herein, is defined as the ratio of the total volume of the device 196, 296 to the flow rate of the cell culture fluid 198 through the device 196, 296. The residence time for the device 296 may range from around 10 minutes to 40 minutes or within smaller ranges, such as from 16 minutes to 30 minutes, from 23 minutes to 27 minutes, or any other suitable range or combination of such ranges. This range of residence time of the cell culture fluid 198 within the device 296 allows for efficient settling of the particles to provide a substantially clarified fluid layer 202 within an efficient separation time period. Therefore, if a target volume of the cell culture fluid 198 to be processed and a capacity of the device 296 are known, the flow rate of the cell culture fluid 198 can be set or adjusted to provide a target residence time (e.g., 24 minutes, 25 minutes, 26 minutes, and so forth) within the above ranges. The residence time within the above ranges may provide efficient settling of the particles of the cell culture fluid 198, which may be a high cell density cell culture fluid (e.g., 1 million to 20 million cells/mL), and clarifying of the fluid layer 202 of the cell culture fluid 198 within a manageable time period, as discussed in greater detail with reference to Tables 4 and 5. As such, the device 296 may be scalable to a target volume to be processed and/or to a particular harvest application.

Figure 9:
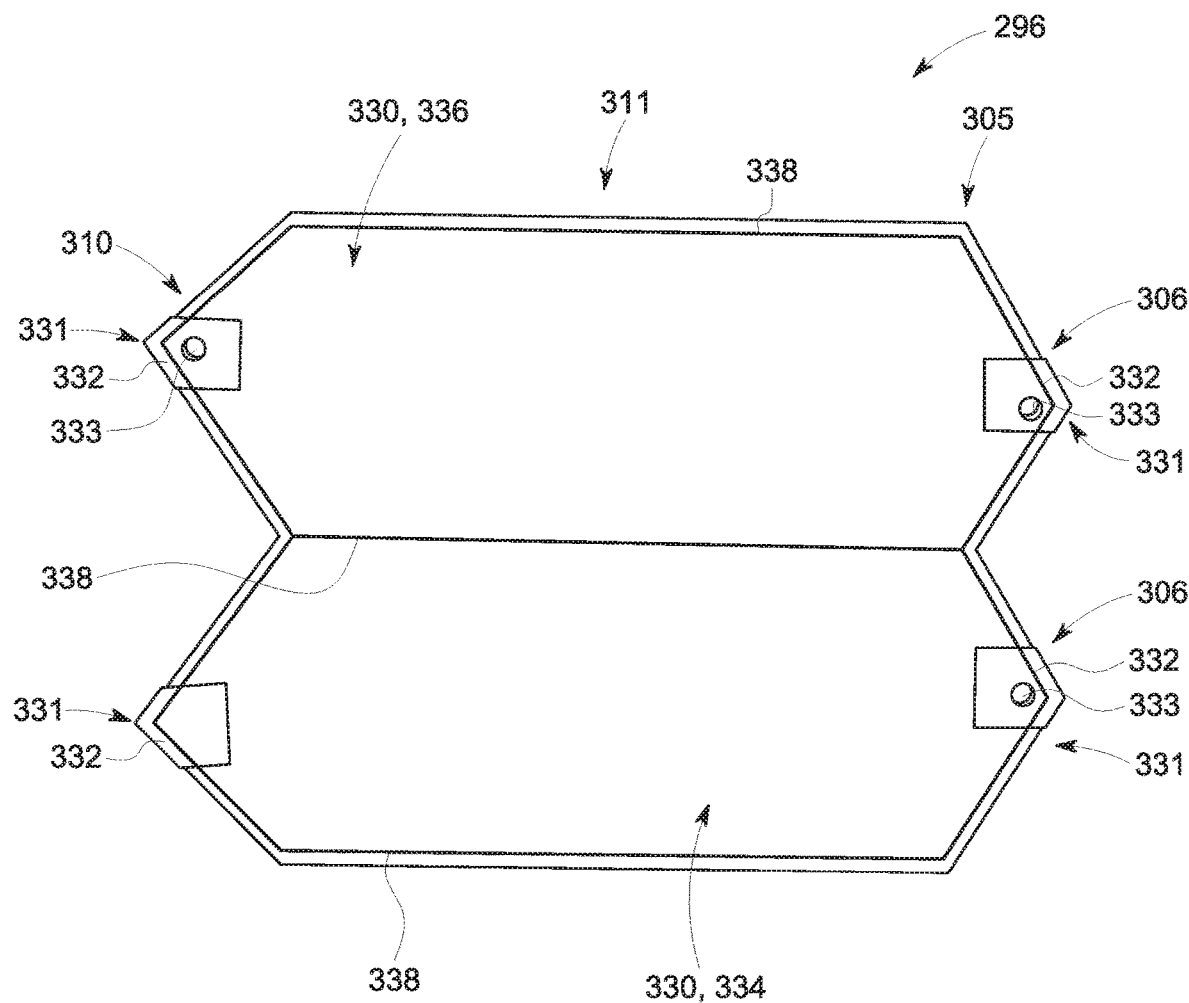
FIG. 9 illustrates a schematic representation of a partially exploded view of an embodiment of the separation device of FIG. 8 showing layers of the separation device, in accordance with aspects of the present disclosure.

FIG. 9 illustrates a partial exploded view of the separation device 296 showing two layers 330 used to form the device 296. The device 296 may be formed from perimeter-bonded layers 330 of biocompatible film or polymer. Each layer 330 may have a chevron shape, as shown in the illustrated embodiment, or other polygonal shape. As such, the layers 330 may be angled toward the fluid inlet manifold 306 and the fluid outlet manifold 310. Each end 331 of each layer 330 includes a spacer 332, which may be made of a thicker material than the layers 330. Some of the spacers 332 may include a hole 333 through the spaces 332, which is made during fabrication. The spacers are heat-welded to the each end 331 of the layers 330. The holes 333 of the spacers 332 form manifolds (e.g., conduits) when the layers are perimeter-bonded into the device 296, and the space between the spacers 332 form the mesofluidic channels 308.

The device 296 may include a bottom layer 336, one or more intervening layers 336, and a top layer (not shown). The illustrated embodiment shows the bottom layer 334 bonded along one side to one intervening layer 336 via a perimeter bond 338. The bottom layer 336 and the top layer may each include only one spacer 332 having the hole 333, while the intervening layers 336 each include spacers 332 having the hole 333 on both ends 331 of the layers 336. The bottom layer 334 may include one spacer 332 with the hole 333 at one end 331 of the bottom layer 334 and may include one spacer 332 without the hold 333 at the opposite end 331 of the bottom layer 334. The top layer may also include one spacer 332 with the hole 333 at one end 331 and may include one spacer 332 without the hold 333 at the opposite end 331, however the spacer 332 including the hole 333 of the bottom layer 334 is on the opposite end 331 as the spacer 332 including the hole 333 of the top layer. That is, the bottom layer is oriented 180° relative to the top layer. This orientation provides for the fluid inlet manifold 306 and the fluid outlet manifold 310 when the layers 330 are perimeter-bonded together, such that no flow can be directed out of the device 296 without first flowing through the one or more mesofluidic channels 308.

Figure 10:
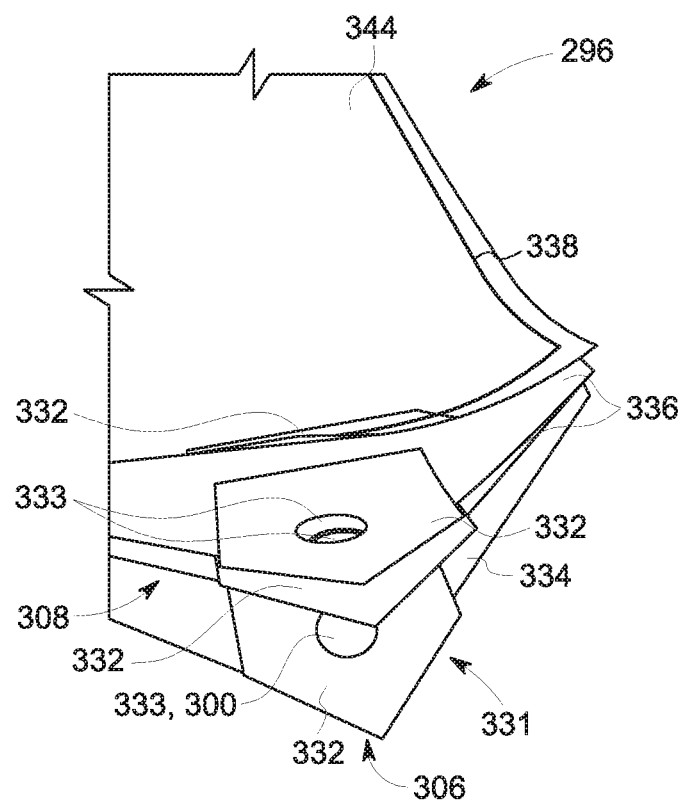
FIG. 10 illustrates a schematic representation of a perspective view of the layers at an inlet of the separation device of FIG. 9, in accordance with aspects of the present disclosure.

FIG. 10 illustrates the layers 330 at the end 331 forming the fluid inlet manifold 306 of the device 296. To form the fluid inlet manifold 306 when the layers 330 are bonded together via the perimeter bond 338, the bottom layer 334 contains the spacer 332 having the hole 333 on the end 331 of the device 296 that includes the fluid inlet manifold 306. A top layer 344 contains the spacer 332 without the hole 333 on the end 331 of the device 296 that includes the fluid inlet manifold 306, and the one or more intervening layers 336 contain the spacer 332 having the hole 333 on the end 331 of the device 296 that includes the fluid inlet manifold 306. As such, when the layers 330 are perimeter-bonded together, the hole 333 of the bottom layer 334 is the fluid inlet 300 of the device 296 and the stacked mesofluidic channels 308 are formed between the layers 330. For example, in the illustrated embodiment, the device 296 contains three mesofluidic channels 308 formed between the bottom layer 334 and the adjacent intervening layer 336, between the two intervening layers 336, and between the top layer 344 and the adjacent intervening layer 336.

In operation, the cell culture fluid 198 may be flowed into the device 296 via the fluid inlet 300 and into the fluid inlet manifold 306. The cell culture fluid 198 may only enter the mesofluidic channels 308 in the direction of the flow into the device 296 because the spacer 332 without the hole 333 of the top layer 344 will block the flow from continuation in the fluid inlet manifold 306. The fluid inlet manifold 306 will substantially equally distribute the cell culture fluid 198 between the mesofluidic channels.

Figure 11:
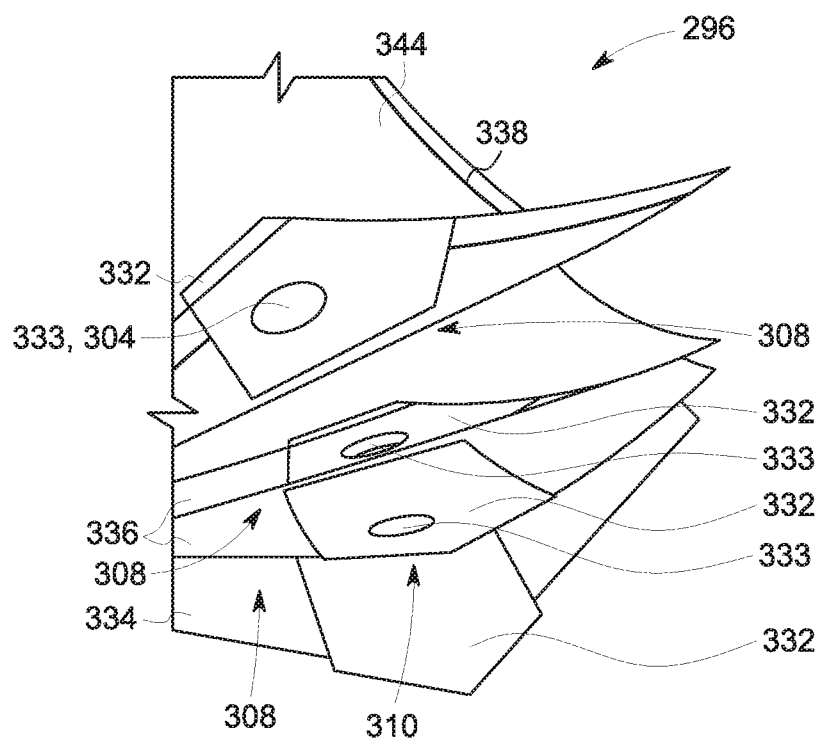
FIG. 11 illustrates a schematic representation of a perspective view of the layers at an outlet of the separation device of FIG. 9.

FIG. 11 illustrates the layers 330 at the end 331 forming the fluid outlet manifold 310 of the device 296. To form the fluid outlet manifold 310 when the layers 330 are bonded together via the perimeter bond 338, the top layer 344 contains the spacer 332 having the hole 333 on the end 331 of the device 296 that includes the fluid outlet manifold 310.

The bottom layer 334 contains the spacer 332 without the hole 333 on the end 331 of the device 296 that includes the fluid outlet manifold 310, and the one or more intervening layers 336 contain the spacer 332 having the hole 333 on the end 331 of the device 296 that includes the fluid inlet manifold 310. As such, when the layers 330 are perimeter-bonded together, the hole 333 of the top layer 344 is the fluid outlet 304 of the device 296 and the stacked mesofluidic channels 308 are formed between the layers 330. For example, in the illustrated embodiment, the device 296 contains three mesofluidic channels 308 formed between the bottom layer 334 and the adjacent intervening layer 336, between the two intervening layers 336, and between the top layer 344 and the adjacent intervening layer 336.

In operation, after the cell culture fluid 198 is flowed through the mesofluidic channels 308 of the device 296 to allow the cells and/or particles to separate from the base fluid layer, the clarified fluid layer 202 may exit the mesofluidic channels 308 and flow into the fluid outlet manifold 310. The fluid outlet manifold 310 may collect the clarified fluid layer 202 flowed from each mesofluidic channel 308 and may direct the clarified fluid layer 202 out of the deice 296 via the fluid outlet 304 in the spacer 332 of the top layer 344. As such, the cells and/or other particles that fell out of the cell culture fluid 198 may remain within the mesofluidic channels 308 formed from the perimeter-bonded layers 330 and the clarified cell culture fluid 202 may be recovered from the fluid outlet of the device 296.

Figure 12:
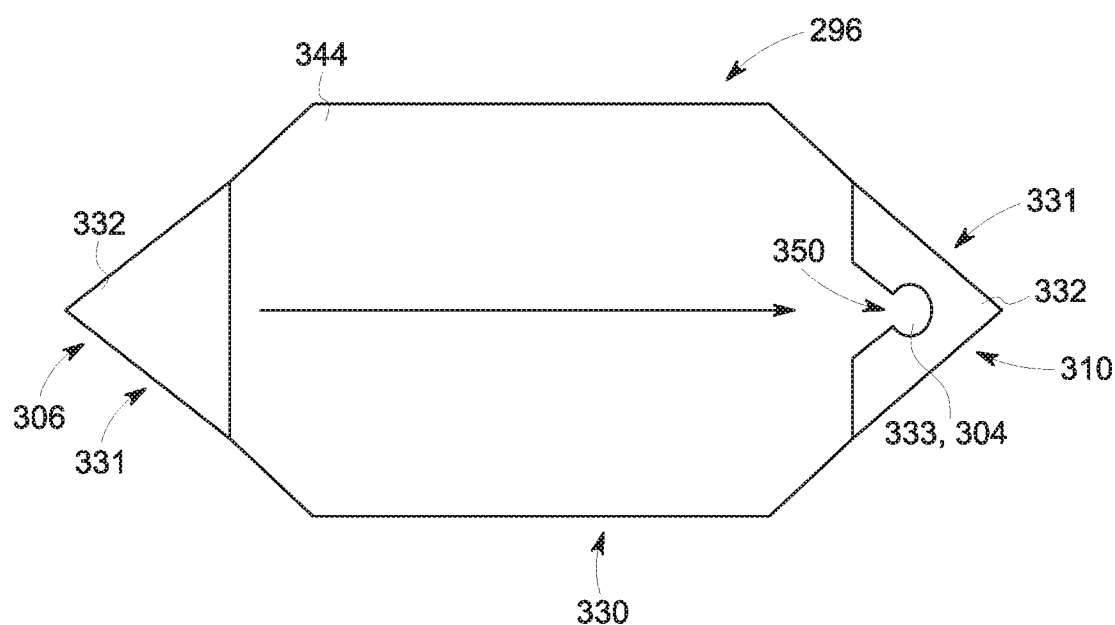
FIG. 12 illustrates a schematic representation of a top view of the separation device of FIG. 9, in accordance with embodiment of the present disclosure.

FIG. 12 illustrates a top view of an embodiment of the device 296. As previously discussed, the spacer 332 of the top layer 344 which forms part of the fluid inlet manifold 306 does not include the hole 333, while the spacer 332 of the top layer 344 which forms part of the fluid outlet manifold 310 includes the hole 333, which also forms the fluid outlet 304 of the device 296. In some embodiments, the holes 333 of the spacers 332 may include a partial gap 350 to increase ease of flow from the fluid inlet manifold 306 into the one or more mesofluidic channels 308 and into the fluid outlet manifold 310 from the one or more mesofluidic channels 308. The spacers 332 may be thicker than the material of the layer 330. As such, a thickness of the spacers 332 may define the height of each mesofluidic channel 308. Additionally, in some embodiments, one or more plates may be aligned with the spacers at the fluid inlet channel 306 and/or the fluid outlet channel 310 above and/or below the device 196 to compress the spacers to a particular predefined mesofluidic channel height.

Experimental conditions and results of processing of cell culture fluid using three embodiments of the separation device (e.g., separation devices 196 and 246) are shown in Table 4 above and Table 5 below. The cell culture fluid 198, in this case a CHO cell suspension, was processed through a device having five relatively wide mesofluidic channels disposed in a series stack, a device having five relatively narrow mesofluidic channels disposed in a series stack, and a device having only one flexible mesofluidic channel (discussed in greater detail with reference to FIG. 20).

An internal monoclonal CHO cell line modified to produce a mAb (Hyclone CHO producing Herceptin) was grown in ActiPro media in various cultures. 500 mL shake flasks (150 rpm, 7.5% CO2, 37 C) were used to achieve 10-20 million cells per mL whereas higher cell densities (30-40 million cells/mL) were cultured in a fed batch 10 L stirred tank reactor (BioFlow 310: 150 rpm, pH, DO, and temp control). Concentrated cell densities above 40 million cells/mL were obtained via centrifugation of harvested cells into a pellet and resuspending in reduced volumes with spent media. The container holding the cells for harvesting was always stirred to insure homogenous cell densities. Several sized separation devices were used for separation. In all cases, a peristaltic pump (Cole Parmer Master Flex L/S, with either Easy load (Model 7517-00) or Easy Load II (model 77202-60) pump heads) was used to negatively displace the cells from the reactor into the tubing and then positively displace cells into the harvester. To avoid variable cell settling in the tube between the pump and harvester, the tubing distance was minimized as much as possible and kept level. Additionally, if the separation device had multiple fluid inlets or outlets, care was taken to level the fluid inlet manifolds and the fluid outlet manifolds such that even flow would enter and exit each of the ports.

As shown in Table 4, the device having five relatively wide mesofluidic channels disposed in a series stack (e.g., wide 5 stack) had a device volume of 2,000 L and the flow rate of the cell culture fluid through the device of 85.7 mL/min, thus resulting in a residence time of the cell culture fluid within the device of 23.3 minutes. The device having five relatively narrow mesofluidic channels disposed in a series stack had a device volume of 200 mL and the flow rate of the cell culture fluid through the device of 7.9 mL/min, thus resulting in a residence time of the cell culture fluid within the device of 25.4 minutes. Further, device having only one flexible mesofluidic channel had a device volume of 65 mL and the flow rate of the cell culture fluid through the device of 2.7 mL/min, thus resulting in a residence time of the cell culture fluid within the device 196 of 24.1 minutes.

EXAMPLES

TABLE 4

Experimental conditions for processing cell culture fluid using three different size devices.

| Experimental Conditions | | Wide 5 Stack | Narrow 5 Stack | Film Single | Narrow 5 Stack | Narrow 5 Stack | Narrow 5 Stack w/ 0.03 wt % pDADMAC |
|---|---|---|---|---|---|---|---|
| Process Angle | Degrees | 5 | 5 | 12.5 | 5 | 5 | 25 |
| Target Flow Rate | mL/min | 86 | 8 | 2.6 | 8 | 8 | 8 |
| Actual Flow Rate | mL/min | 85.7 | 7.9 | 2.7 | 7.9 | 7.9 | 7.9 |
| Device Volume | mL | 2,000 | 200 | 65 | 200 | 200 | 200 |
| Residence Time | min | 23.3 | 25.4 | 24.1 | 25.4 | 25.4 | 25.4 |
| Feed Cell Concentration | cells/mL | 42M | 42M | 42M | 28M | 57M | 50M |
| Feed Viability | % | 99.6 | 99.6 | 99.6 | 39.7% | 17.1% | 48.6% |
| Feed Turbidity | NTU | 1,592 | 1,592 | 1,592 | 2,140 | 2,889 | 7,064 |

TABLE 5

Empirical results for cell culture processing using three different size devices.

| Experimental Results | | Wide 5 Stack | Narrow 5 Stack | Film Single | Narrow 5 Stack | Narrow Stack | Narrow 5 Stack |
|---|---|---|---|---|---|---|---|
| pDADMAC | Wt % | 0 | 0 | 0 | 0 | 0 | 0.03 |
| Effluent Turbidity | NTU | 77.3 | 69.1 | 64.6 | 139 | 242.5 | 3.89 |
| Effluent Cell Concentration | MM/mL | 0.66M | 0.044M | 0.11M | 0.90M | 1.44M | <LOD |
| Total Cells Captured | MM | 24,6147 | 58,711 | 16,684 | 24,040 | 23,734 | 19,750 |
| % Cells Captured | % | 97.2 | 99.9 | 98.3 | 97 | 97.5 | ~100% |
| Volume Processed | mL | 6001 | 1412 | 402 | 986 | 487 | 395 |

These processing conditions show that the device may have a capacity or device volume of up to 2,000 L that may be processed at time. As shown in Table 5, each of the devices described efficiently separate the particles (e.g. cells) from the fluid layer of the cell culture fluid and provide a retention of the cells within the device between 97.2%-99.9%. As such, the residence time for each device 196, within the range previously discussed with reference to FIG. 2, was able to efficiently clarify the cell culture fluid that was provided to each device, at a particular residence time within the previously discussed ranges when provided the cell culture medium and a particular flow rate relative to the device capacity. Thus, the device may provide cell removal from the cell culture fluid 198 at retention rates similar to centrifugation, but with a device that is simpler and may be disposable.

While only certain features of the present disclosure have been illustrated and described herein, many modifications and changes will occur to those skilled in the art. It is, therefore, to be understood that the appended embodiments are intended to cover all such modifications and changes as fall within the scope of the disclosure.

The invention claimed is:

1. A method for clarifying a bioprocess fluid comprising particles suspended in a cell culture fluid, the method comprising:
flowing an unclarified bioprocess fluid from a bioreactor through a plurality of mesofluidic channels of a separation device comprising a fluid inlet and fluid outlet to separate at least a portion of particles of the unclarified bioprocess fluid to generate a substantially clarified bioprocess fluid, the substantially clarified bioprocess fluid having more than 80% of the particles removed relative to the unclarified bioprocess fluid; and
collecting the substantially clarified bioprocess fluid from the fluid outlet of the separation device;
wherein a residence time of the bioprocess fluid between the fluid inlet and fluid outlet of the separation device ranges from 10 minutes to 40 minutes, and wherein the separation device is operated at an angle less than 10° relative to a work surface thereby allowing the particles to settle and collect on a lower interior surface of each mesofluidic channel.

2. The method of claim 1, wherein the separation device is operated at an angle less than or equal to 5° relative to the work surface.

3. The method of claim 1, wherein the separation device is operated at an angle of about 0° relative to the work surface.

4. The method of claim 1, wherein the particles comprise cells, aggregated cells, adhered cells on carriers, diatomaceous earth, resin beads, or a combination thereof.

5. The method of claim 1, wherein the substantially clarified bioprocess fluid comprises biotherapeutically active products, cells, viruses, vaccines, DNA, RNA, or a combination thereof.

6. The method of claim 1, wherein a capacity of the separation device and a flow rate of the bioprocess fluid flowed through the plurality of mesofluidic channels is configured to process up to 10,000 liters of the bioprocess fluid within the residence time.

7. The method of claim 1, wherein a capacity of the separation device and a flow rate of the bioprocess fluid flowed through the plurality of mesofluidic channels is configured to process up to 4,000 liters of the bioprocess fluid within the residence time.

8. The method of claim 1, wherein a capacity of the separation device and a flow rate of the bioprocess fluid flowed through the plurality of mesofluidic channels is configured to process up to 2,000 liters of the bioprocess fluid within the residence time.

9. The method of claim 1, additionally comprising recovering the separated particles from the plurality of mesofluidic channels of the separation device subsequent to collecting the clarified bioprocess fluid.

10. The method of claim 1, additionally comprising adding a flocculant to the unclarified bioprocess fluid before flowing the unclarified bioprocess fluid through the separation device to aid in separation of the particles from the bioprocess fluid.

11. The method of claim 1, additionally comprising:
lowering the pH of the unclarified bioprocess fluid before flowing the unclarified bioprocess fluid through the separation device, and
raising the pH of the clarified bioprocess fluid to a neutral pH after collecting the clarified bioprocess fluid from the separation device.

12. The method of claim 1, additionally comprising flushing the separation device before a terminal capacity of the separation device is reached, wherein flushing the separation device comprises flowing a separate fluid through the separation device and removing the particles separated in the separation device.

13. The method of claim 1, additionally comprising reversing a flow from the outlet of the separation device such that a separate fluid is flowed from the fluid outlet of the separation device to the fluid inlet of the separation device before a terminal capacity of the separation device is reached, and returning the separated particles to the bioreactor or a separate container.

14. The method of claim 1, additionally comprising recovering the separated particles captured in the separation device.

15. The method of claim 1, wherein the separation device is intermittently tilted to the angle to evacuate air from the mesofluidic channels.

16. A system for isolating a target molecule from a bioprocess fluid according to the method of claim 1, the system comprising:
- a single-use disposable separation device comprising a plurality of perimeter-bonded layers defining one or more mesofluidic channels of the separation device, wherein each of the plurality of perimeter-bonded layers comprises a biocompatible polymer material, wherein the separation device is configured to separate at least a portion of particles from the bioprocess fluid to generate a substantially clarified bioprocess fluid; and
- a secondary purification system fluidically coupled to and outlet of the separation device configured to further process the clarified bioprocess fluid.

17. The system of claim 16, wherein the plurality of perimeter-bonded layers comprise a top layer, a bottom layer, and one or more intervening layers, and wherein the plurality of perimeter-bonded layers define the one or more mesofluidic channels in a stacked parallel configuration.

18. The system of claim 17, wherein the separation device comprises a plurality of spacers disposed at ends of each of the plurality of perimeter-bonded layers, wherein the spacers of each of the one or more intervening layers comprises a hole, wherein each of the top layer and the bottom layer comprise one spacer comprising a hole and one spacer not comprising a hole, and wherein the spacer of the top layer comprising the hole is disposed at an end of the device opposite the spacer of the bottom layer comprising the hole.

19. The system of claim 18, wherein the separation device comprises a fluid inlet manifold and a fluid outlet manifold, wherein the fluid inlet and the fluid outlet are formed from the holes of the spacers, and wherein the one or more mesofluidic channels are fluidically coupled to and disposed between the fluid inlet manifold and the fluid outlet manifold.

20. The system of claim 19, wherein each mesofluidic channel of the one or more mesofluidic channels of the separation device comprise a height within a range of 2 millimeters to 20 millimeters, and wherein the height of each mesofluidic channel is defined by the spacers.

21. The system of claim 16, comprising a bioreactor fluidically coupled to an inlet of the separation device and configured to flow the bioprocess fluid to the separation device.

22. The system of claim 16, wherein the separation device comprises a capacity of up to 2,000 L such that when the separation device is provided with the bioprocess fluid at a particular flow rate, a ratio of the capacity of the separation device to the flow rate of the provided bioprocess fluid is within a range of 10 minutes to 40 minutes.

23. The system of claim 16, wherein the separation device comprises multiple separation devices connected in parallel or in series.

24. The system of claim 16, wherein the separation device comprises multiple separation devices connected in parallel which are fluidically coupled to the bioreactor, and wherein the parallel separation devices are operated in an alternating arrangement such that the parallel separation devices can be alternately supplied with the bioprocess fluid.

25. The system of claim 16, wherein a residence time of the bioprocess fluid within the separation device ranges from 10 minutes to 40 minutes.

26. The system of claim 16, wherein the secondary purification system includes depth filtration, membrane filtration, chromatography, centrifugation, or any combination thereof.

27. A system for isolating a target molecule from a bioprocess fluid according to the method of claim 1, the system comprising:
- a bioreactor;
- a separation device fluidically coupled to the bioreactor at an inlet of the separation device and configured to receive a flow of the bioprocess fluid from the bioreactor and to separate a least a portion of particles from the bioprocess fluid to generate a substantially clarified bioprocess fluid, wherein the separation device comprises a plurality of parallel mesofluidic channels for separation of the particles, and wherein the separation device is operated at an angle less than 10° relative to a work surface; and
- one or more additional purification subsystems fluidically coupled to an outlet of the separation device and configured for further processing of the clarified bioprocess fluid, wherein the additional purification subsystems comprise chromatographic separation, secondary depth filtration, a polishing membrane, or any combination thereof.

28. The system of claim 27, wherein the separation device is a configured to process the bioprocess fluid having a cell density of at least 1 million cells/mL.

29. The system of claim 27, wherein a residence time of the bioprocess fluid within the separation device ranges from 16 minutes to 30 minutes.

* * * * *